United States Patent
Bidwell et al.

[11] Patent Number: 6,007,521
[45] Date of Patent: Dec. 28, 1999

[54] DRAINAGE CATHETER SYSTEM

[76] Inventors: Robert E. Bidwell, 27 Montrose Pl., Melville, N.Y. 11847; Arnold Melman, 23 Agnes Circle, Ardsley, N.Y. 10502

[21] Appl. No.: 08/779,562

[22] Filed: Jan. 7, 1997

[51] Int. Cl.$^6$ .................................................. A61M 5/00
[52] U.S. Cl. ............................ 604/264; 604/96; 604/317; 604/349; 604/351; 604/353
[58] Field of Search ............................... 604/96, 264, 265, 604/267, 200, 317, 327, 339, 343, 345, 344, 349, 351, 353, 406, 400, 403, 352, 171, 172, 174, 175, 176, 177, 178, 179, 180; 128/760, 767, 761

[56] References Cited

U.S. PATENT DOCUMENTS

| | | |
|---|---|---|
| 3,053,257 | 9/1962 | Birtwell . |
| 3,168,092 | 2/1965 | Silverman . |
| 3,169,527 | 2/1965 | Sheridan . |
| 3,500,819 | 3/1970 | Silverman . |
| 3,583,391 | 6/1971 | Cox et al. . |
| 3,589,356 | 6/1971 | Silverman . |
| 3,669,099 | 6/1972 | Silverman . |
| 3,683,928 | 8/1972 | Kuntz et al. . |
| 3,726,281 | 4/1973 | Norton et al. . |
| 3,853,130 | 12/1974 | Sheridan . |
| 3,897,785 | 8/1975 | Barto, Jr. . |
| 4,073,295 | 2/1978 | Laufbahn . |
| 4,271,839 | 6/1981 | Fogarty et al. . |
| 4,318,947 | 3/1982 | Joung . |
| 4,511,358 | 4/1985 | Johnson, Jr. et al. . |
| 4,539,234 | 9/1985 | Sakamoto et al. . |
| 4,606,347 | 8/1986 | Fogarty et al. . |
| 4,686,124 | 8/1987 | Onohara et al. . |
| 4,713,066 | 12/1987 | Komis . |
| 4,713,067 | 12/1987 | Rothenberg et al. . |
| 4,767,405 | 8/1988 | Lokken ..................................... 604/51 |
| 4,804,377 | 2/1989 | Hanifl et al. ............................ 604/352 |
| 4,810,543 | 3/1989 | Gould et al. . |
| 4,828,554 | 5/1989 | Griffin . |
| 4,846,816 | 7/1989 | Manfredi . |
| 4,863,440 | 9/1989 | Chin . |
| 4,976,703 | 12/1990 | Franetzki et al. . |
| 5,013,306 | 5/1991 | Solomon et al. . |
| 5,013,717 | 5/1991 | Solomon et al. . |
| 5,026,607 | 6/1991 | Kiezulas . |
| 5,032,118 | 7/1991 | Mason . |
| 5,098,379 | 3/1992 | Conway et al. . |
| 5,147,341 | 9/1992 | Starke et al. . |
| 5,171,305 | 12/1992 | Schickling et al. . |
| 5,178,611 | 1/1993 | Rosenberg . |
| 5,179,174 | 1/1993 | Elton . |
| 5,193,553 | 3/1993 | Kalinoski . |
| 5,209,726 | 5/1993 | Goosen . |
| 5,234,420 | 8/1993 | Horton et al. . |
| 5,266,359 | 11/1993 | Spielvogel . |
| 5,269,755 | 12/1993 | Bodicky . |
| 5,269,770 | 12/1993 | Conway et al. . |
| 5,300,032 | 4/1994 | Hibbs et al. . |
| 5,331,027 | 7/1994 | Whitbourne . |
| 5,700,257 | 12/1997 | Minick et al. .......................... 604/408 |
| 5,785,700 | 7/1998 | Olson ...................................... 604/408 |
| 5,792,114 | 8/1998 | Fiore ....................................... 604/171 |

FOREIGN PATENT DOCUMENTS

| | | |
|---|---|---|
| 0227583 | of 1987 | European Pat. Off. . |
| 0247559 | of 1987 | European Pat. Off. . |
| 91/10466 | 7/1991 | WIPO . |

*Primary Examiner*—Corrine McDermott
*Assistant Examiner*—Kent Gring
*Attorney, Agent, or Firm*—Dilworth & Barrese

[57] ABSTRACT

A drainage catheter system including a catheter, a collection bag, and a collection bag saddle, is provided. The catheter includes a catheter body having an interior lumen, an elongate tubular sheath operatively associated with the catheter body, and a layer of lubricant disposed between the catheter body and the tubular sheath. The sheath is inflatable after deployment to provide sealing engagement with an inner wall of the urethra. One end of the catheter body is adapted to be connected to the collection bag which includes a fluid entry portion having a one-way fluid valve, a gas separation chamber, and a one-way gas valve. The collection bag also includes a main liquid reservoir in fluid communication with the fluid entry portion and a sealed drainage member for permitting drainage of the main liquid reservoir. The collection bag saddle facilitates attachment of the collection bag to a patient's body, and includes a main body portion, a plurality of mounting pads attached thereto including adhesive backings, and collection bag mounting structure formed in the main body portion.

29 Claims, 21 Drawing Sheets

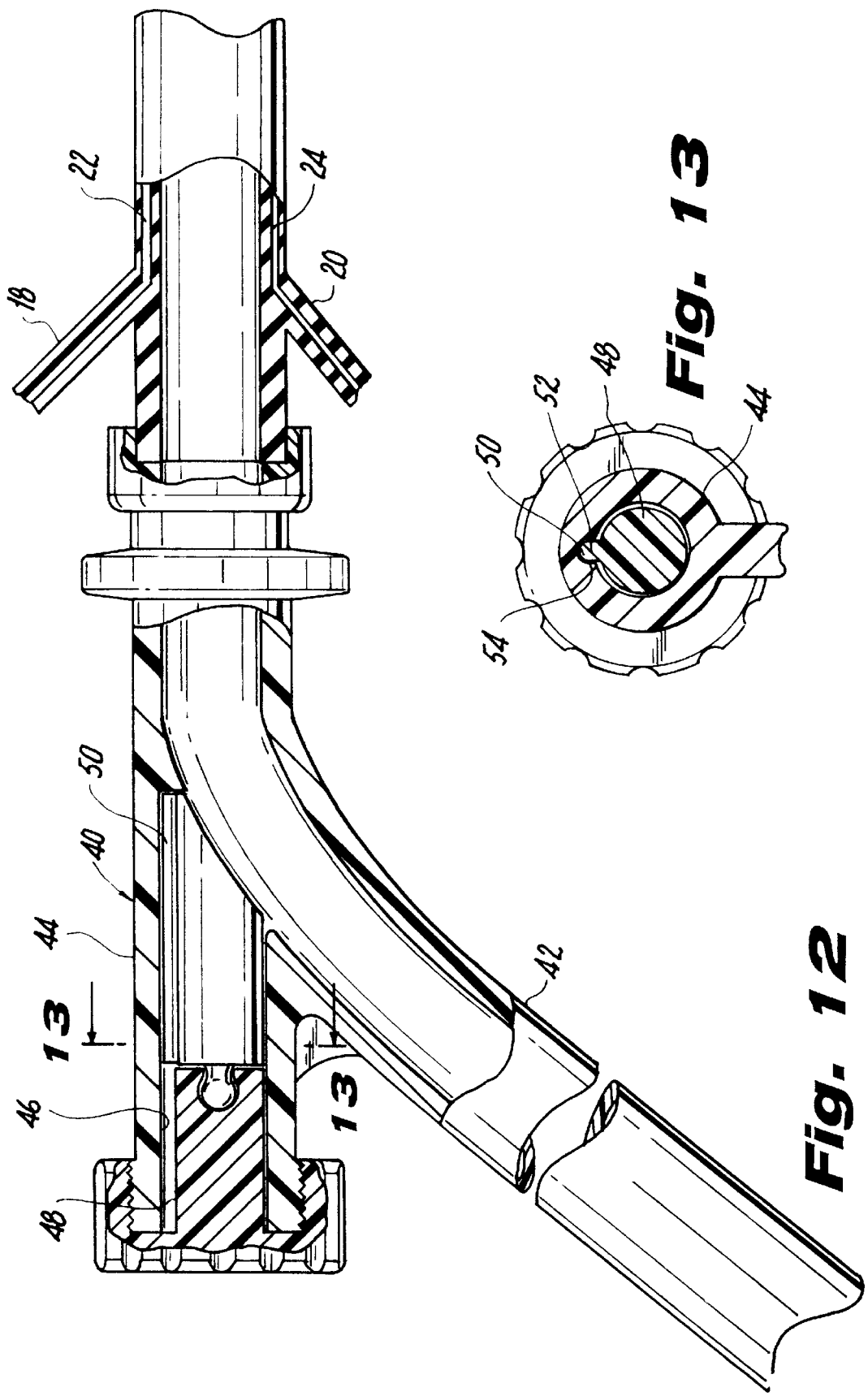

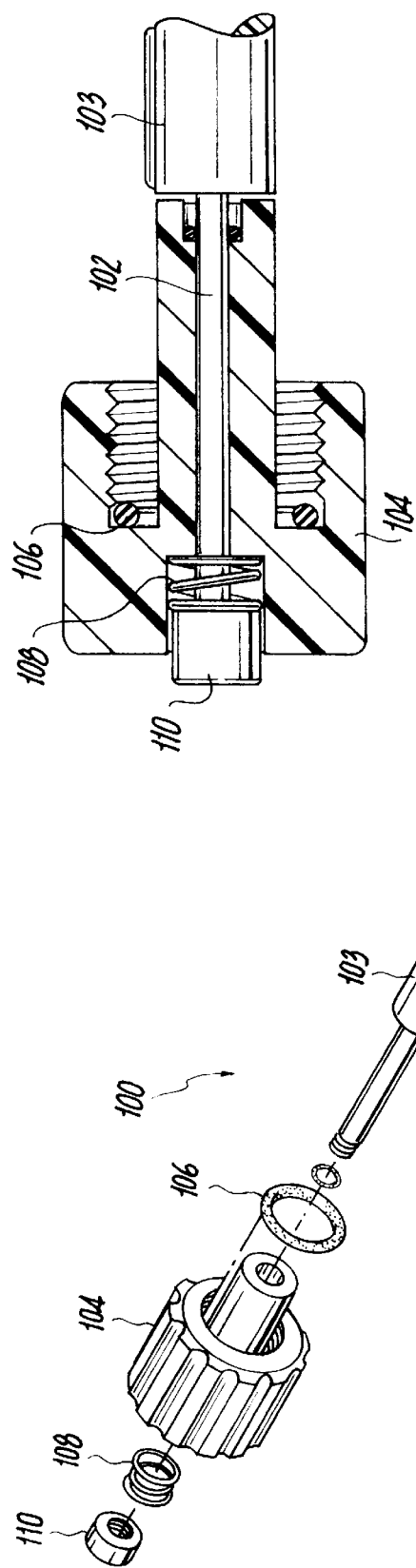
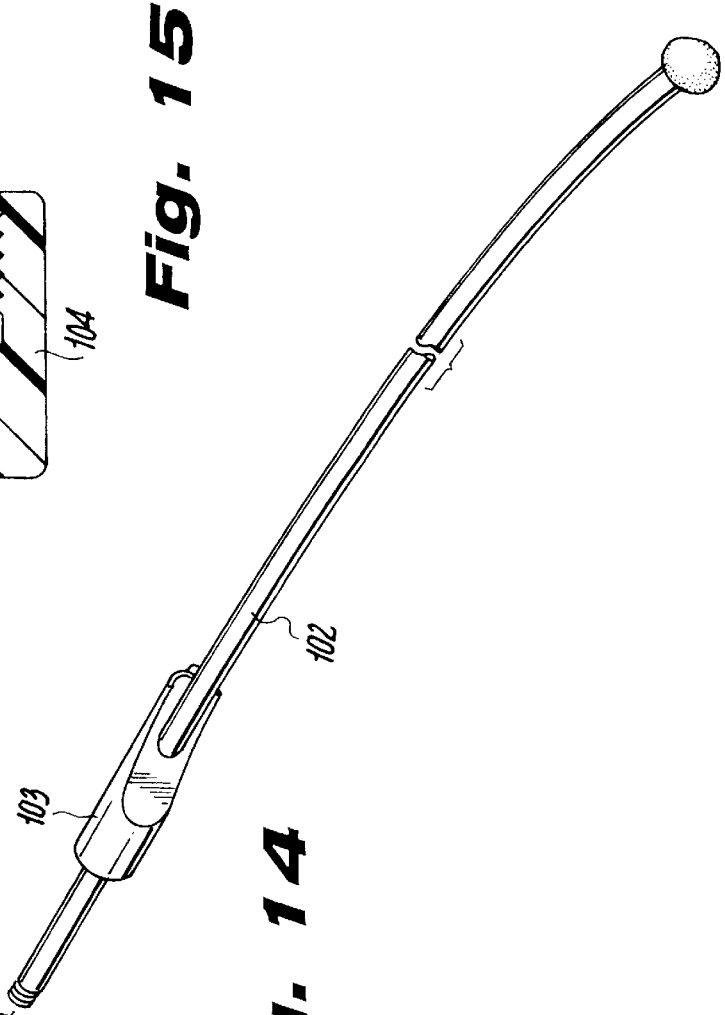
Fig. 15
Fig. 14

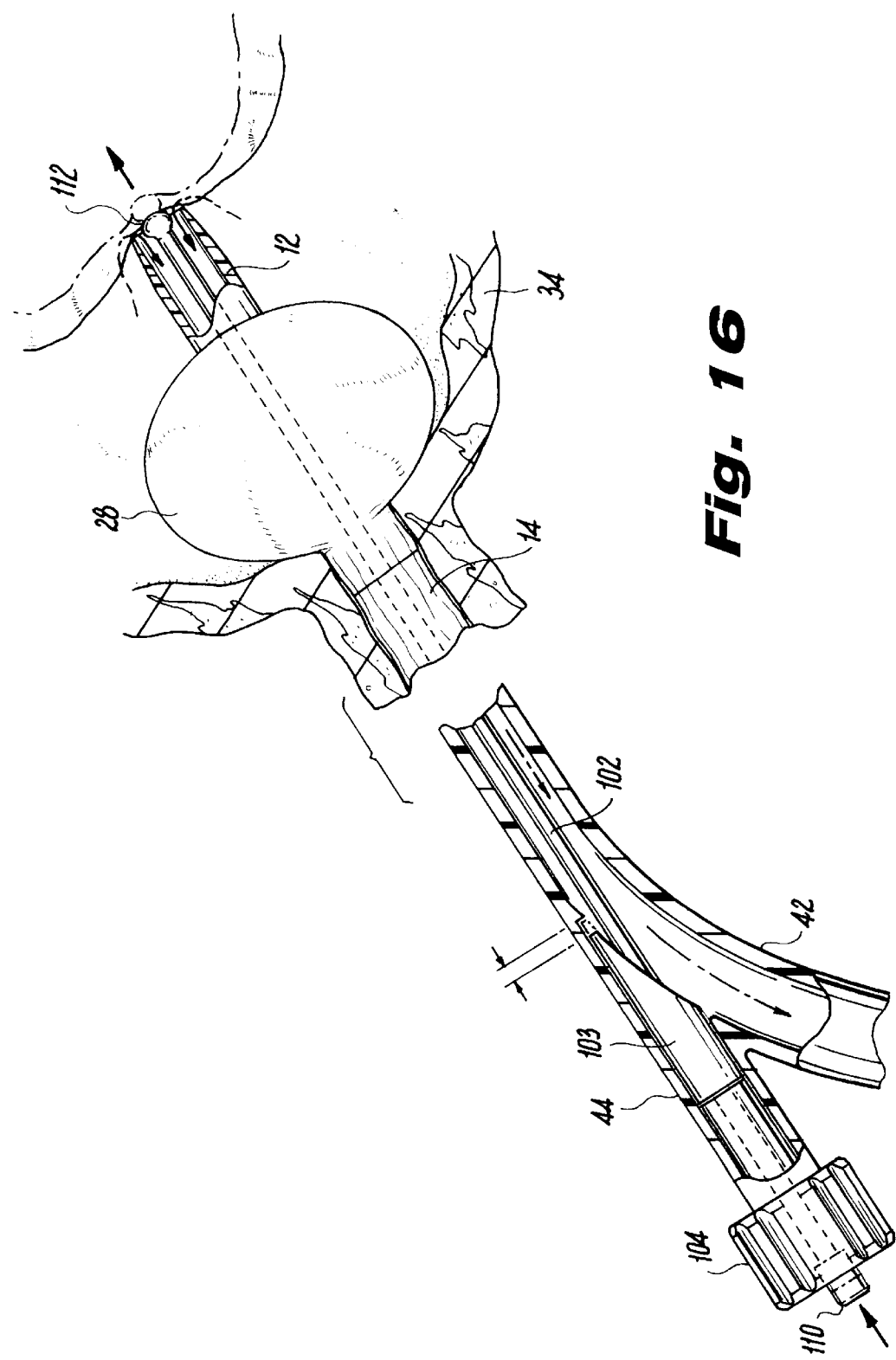

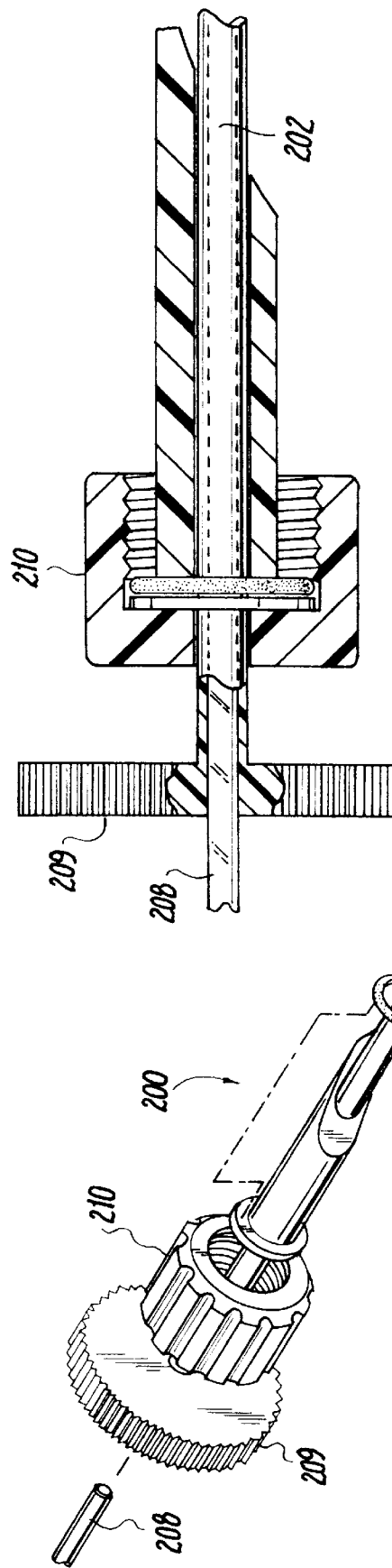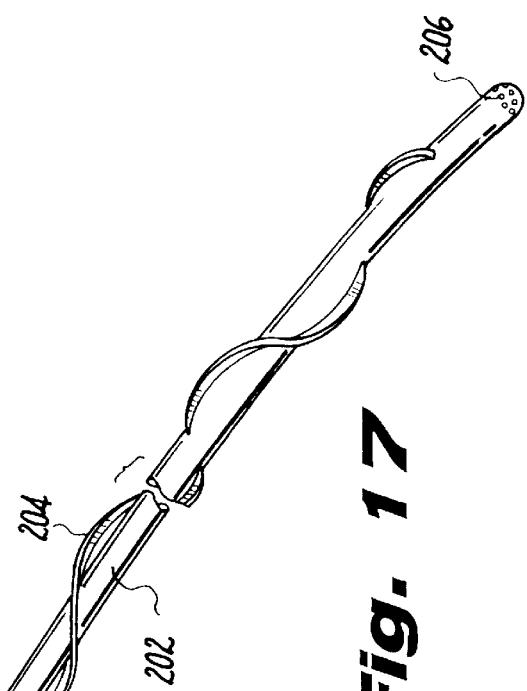

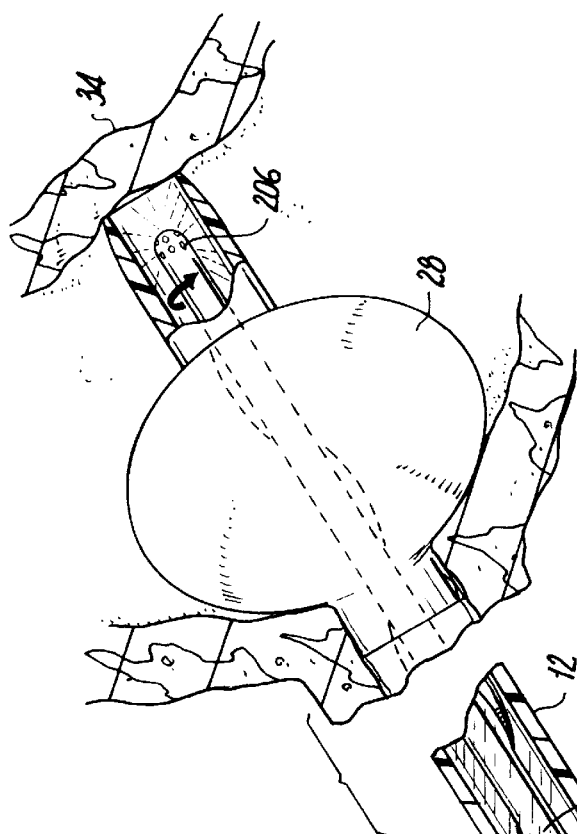
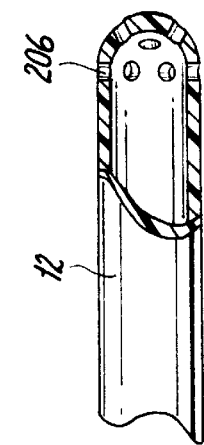
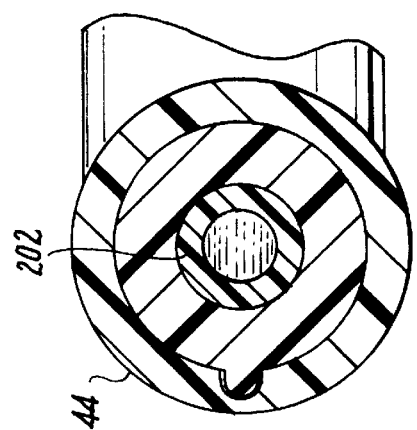
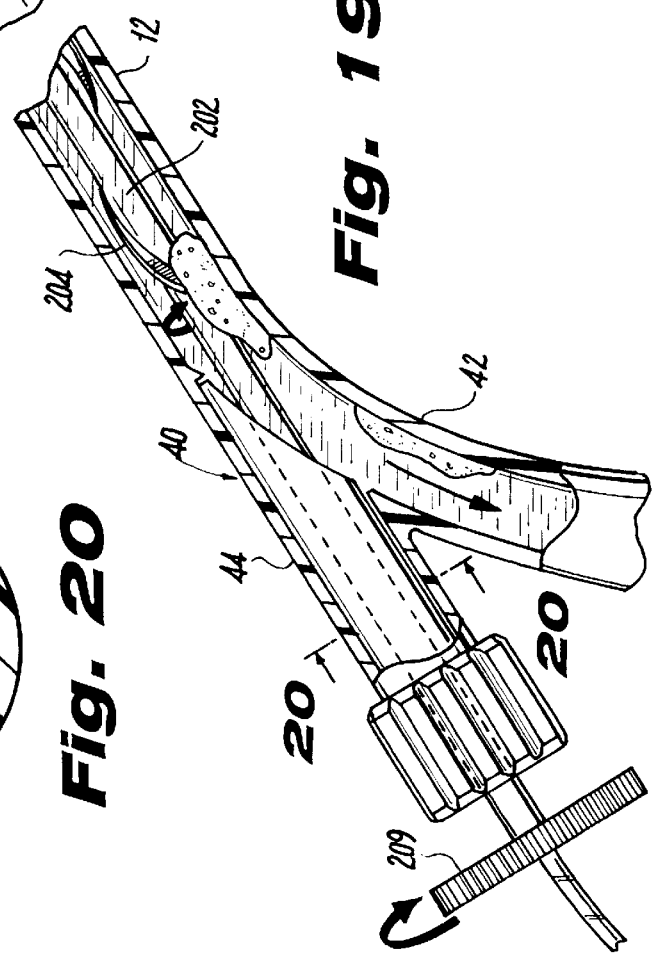
Fig. 19
Fig. 20
Fig. 21

DRAINAGE CATHETER SYSTEM

BACKGROUND OF THE INVENTION

1. Field of the Invention

The subject invention is directed to catheters, and more particularly, to a urinary drainage catheter having a lubricated sheath associated therewith to reduce irritation to the urethra during insertion and removal of the catheter, and while the catheter is positioned therein in a functioning mode.

2. Description of the Related Art

Urethral catheters that are placed within a patient's lower urinary tract are well known in the art. One type of urethral catheter is a retention catheter. Retention catheters are supported in the patient's bladder to continuously remove urine therefrom. One type of urinary retention catheter is known in the art as a Foley catheter. It consists of an elongated tube through which extends a main drain lumen. The catheter is placed through the patient's urethra so that the distal end thereof extends into the patient's bladder and the proximal end remains outside the patient's body. An inlet opening is provided at the distal end of the catheter to allow urine to drain into the main lumen and pass into a collection bag associated with the proximal end of the catheter.

Foley catheters are retained within the patient's bladder and urethra by an inflatable balloon located at the distal end of the elongated tube proximate to the inlet opening of the main lumen. An inflation lumen connects the balloon to the proximal end of the catheter so that a liquid may be passed under pressure to the balloon to expand the balloon. A valve is generally provided to maintain the liquid under pressure so that the balloon remains inflated.

Often, a urinary catheter will remain within the urethra for years at a time, presenting general discomfort to the patient. Such discomfort will be heightened when there is relative movement between the catheter and the urethra. This discomfort results from friction between the outer wall of the catheter and the inner wall of the urethra, and is magnified by even minimal movement of the patient. In addition, the internal cardiac rhythm of the body on breathing, turning in bed and walking may create an irritating friction generating movement of the urethra relative to the catheter. This irritation may be compounded by infection, further complicating and lengthening patient recovery. Even greater discomfort will be experienced when the catheter is removed from the urethra after use.

Several prior art devices have been provided to reduce such discomfort through the use of lubricants, as described, for example, in U.S. Pat. Nos. 3,726,281 and 5,098,379. In U.S. Pat. No. 5,209,726, a catheter is disclosed which has an elongated body enclosed by a resilient sleeve which defines a cavity containing a lubricating substance effective to permit the sleeve to slide along the outer surface of the catheter body. Thus, in use, when the catheter body moves in response to movements of the patient's body, the sleeve will move relative to the urethra. However, during insertion and removal of this catheter, significant frictional contact will occur between the sleeve and the urethra, causing considerable discomfort to the patient. The subject invention provides an improvement over these prior art devices.

SUMMARY

The subject invention is directed to a urethral drainage catheter system configured to reduce patient discomfort during insertion, utilization, and removal. The drainage catheter system includes an elongate catheter body having an interior lumen extending therethrough defined by an interior surface and having an exterior surface. An elongate tubular sheath is operatively associated with the catheter body and has opposed first and second ends. The first and second ends of the sheath are supported adjacent the exterior surface of the catheter body. A layer of lubricant is sealingly disposed between the sheath and the catheter body along the interior and exterior surfaces thereof to reduce frictional resistance between the sheath and the catheter body. The drainage catheter prevents discomfort to the patient by eliminating relative movement between the catheter and the urethra because the friction is absorbed by the catheter.

The subject invention is further directed to a closed system collection bag useable with the drainage catheter system. The closed system collection bag includes a fluid entry portion defining a fluid conduit. The conduit has a one-way fluid valve in line to prevent back flow of fluid and a gas separation chamber for venting gas to the atmosphere. The fluid entry portion further includes at least one one-way gas valve for preventing entry of ambient air into the collection bag. A main liquid reservoir is in fluid communication with the fluid entry portion for receiving and storing liquid therein. The collection bag further includes a sealed drainage member in fluid communication with the main liquid reservoir for permitting drainage of the main liquid reservoir.

Finally, the subject invention is also directed to a saddle bag suitable for supporting the collection bag about a body part of a patient. The saddle bag includes a main body portion and a plurality of mounting pads attached to the main body portion. The mounting pads are provided with adhesive backing thereon for adherence to a patient's skin. Collection bag mounting structure is formed in the main body portion for releasably mounting a collection bag thereon.

BRIEF DESCRIPTION OF THE DRAWINGS

Various preferred embodiments are described herein with reference to the drawings, wherein:

FIG. 12 is a partial cross-sectional view of a portion of the proximal end of the drainage catheter system shown in FIG. 1;

FIG. 13 is a cross-sectional view taken along section line 13—13 of FIG. 12;

FIG. 14 is a perspective view with parts separated of an elongated bladder keeper;

FIG. 15 is a side cross-sectional view of the proximal end of the elongated bladder keeper shown in FIG. 14;

FIG. 16 is a side cross-sectional view of the elongated bladder keeper shown in FIG. 14 in conjunction with the drainage catheter of FIG. 1, inserted in a patient's urethra and engaging the bladder;

FIG. 17 is a perspective view of a fluid introduction and clot auger;

FIG. 18 is a side cross-sectional view of the proximal end of the fluid introduction and clot auger shown in FIG. 17;

FIG. 19 is a side cross-sectional view of the fluid introduction and clot auger shown in FIG. 17 in conjunction with the drainage catheter system shown in FIG. 1, inserted in a patient's urethra;

FIG. 20 is a cross-sectional view taken along section lines 20—20 of FIG. 19;

FIG. 21 is a partial cross-sectional view of the distal end of the fluid introduction and clot auger shown in FIG. 17;

DETAILED DESCRIPTION OF PREFERRED EMBODIMENTS

Figure 1:
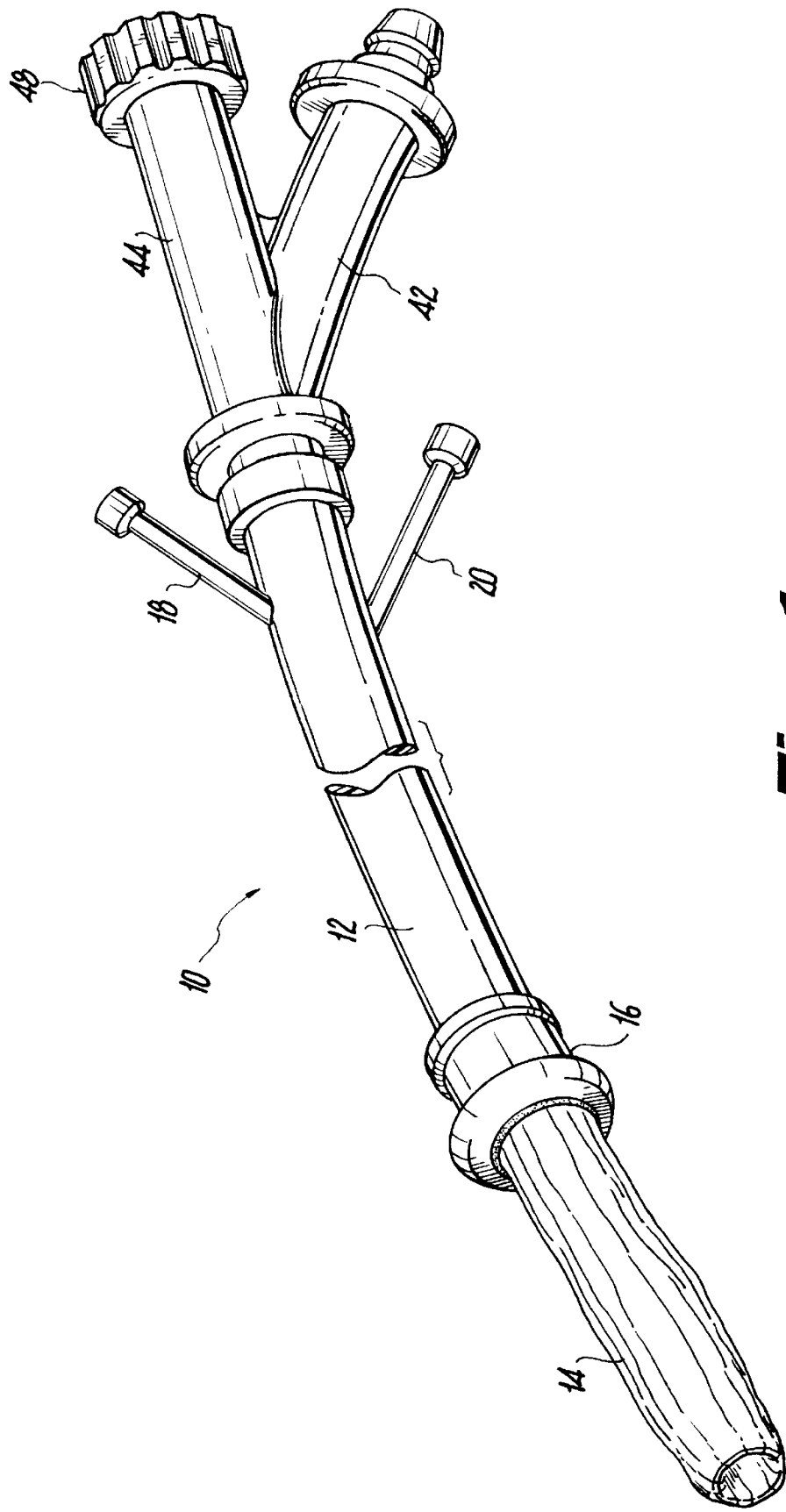
FIG. 1 is a perspective view of one embodiment of the drainage catheter system.

Preferred embodiments of the presently disclosed drainage catheter system will be described in detail with reference to the drawings, in which like reference numerals designate identical or corresponding elements in each of the several views. In the drawings and in the description which follows, the term "proximal", as is traditional, will refer to the end of the surgical apparatus which is closest to the operator, while the term "distal" will refer to the end which is furthest from the operator.

Referring now to the drawings, FIGS. 1–5 illustrate the drainage catheter system of the subject invention shown generally as 10. The system includes a drainage tube 12 dimensioned for insertion into a patient's urethra 13, and a sheath 14 which is attached and sealed about the exterior of the drainage tube 12 to reduce friction during insertion, and eliminate discomfort while the tube is in place for an extended period of time. A sheath grip 16 having a cylindrical throughbore dimensioned to slidably receive drainage tube 12 is fastened to one end of sheath 14. Drainage catheter system 10 also includes first and second inlet tubes 18 and 20 which communicate with first and second lumens 22 and 24, respectively, formed in drainage tube 12. A lubricant 26 is preferably disposed between sheath 14 and the exterior of drainage tube 12 to facilitate sliding movement of tube 12 with respect to sheath 14. A fluid, such as air, liquid or lubricant may also be supplied, via first inlet tube 18 and first lumen 22, to inflate sheath 14 and form a fluid cushion between sheath 14 and the exterior of drainage tube 12. A retention balloon 28 positioned about the distal end of drainage tube 12 communicates with second lumen 24 and may be inflated by connecting a source of pressure to second inlet tube 20.

Figure 6:
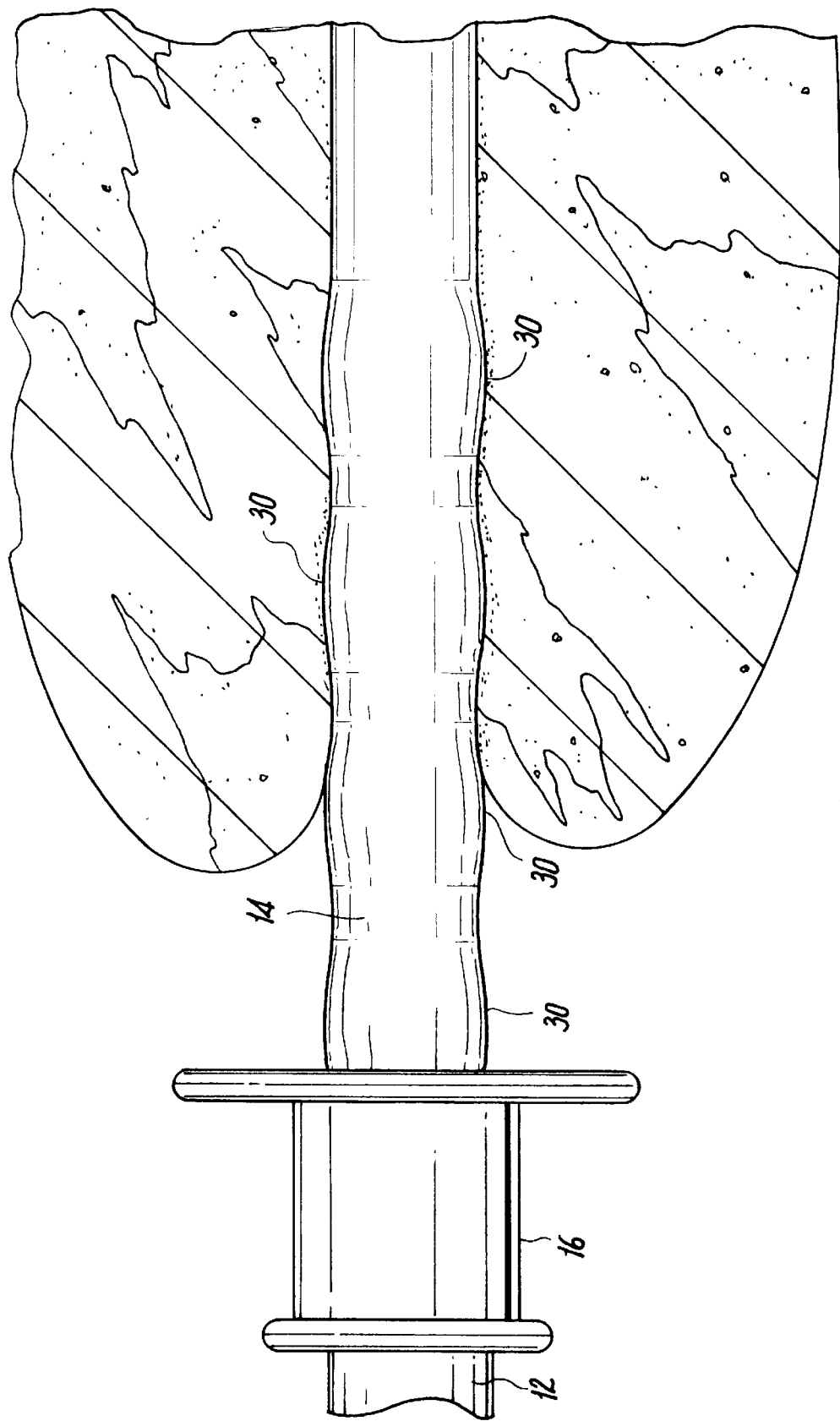
FIG. 6 is a partial side view of the drainage catheter system shown in FIG. 1, including an alternative embodiment of the sheath including a plurality of annular seals.
Figure 7:
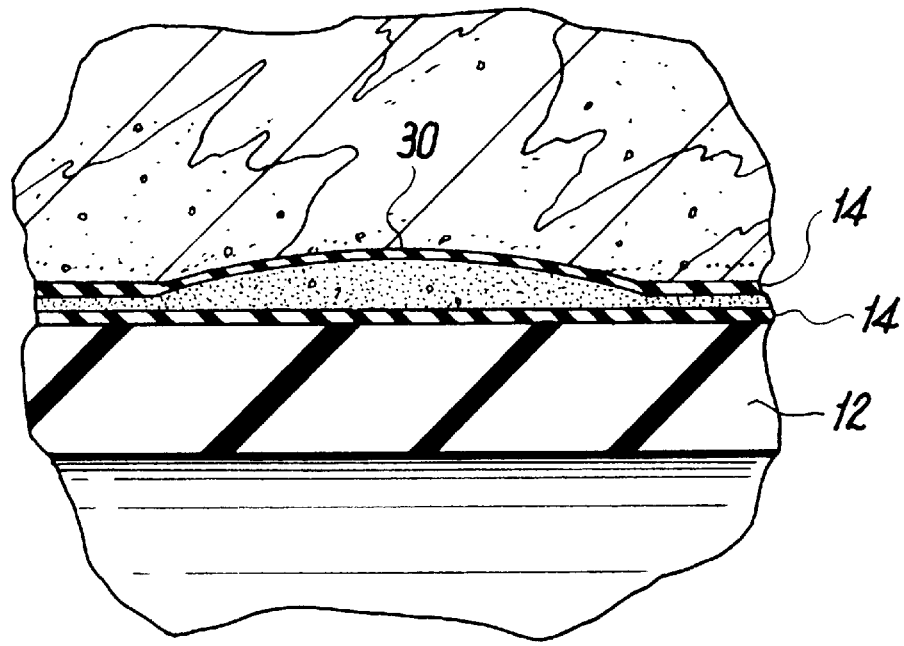
FIG. 7 is a partial cross-sectional view of a portion of the drainage catheter system shown in FIG. 6.
Figure 8:
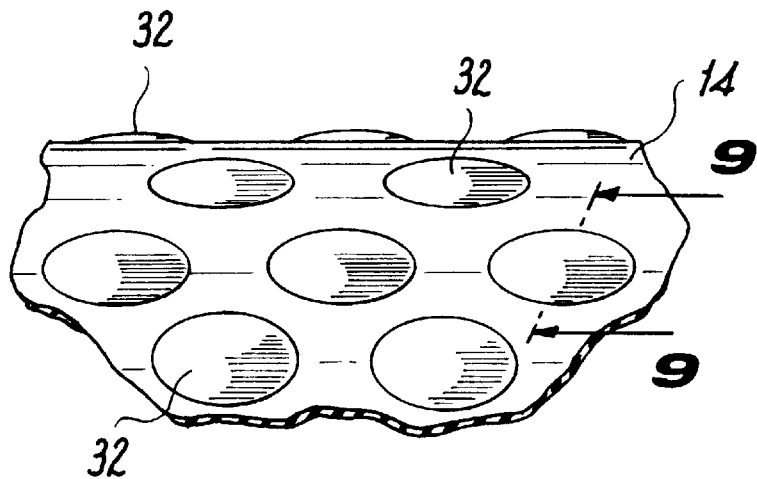
FIG. 8 is a perspective view of an alternative embodiment of the sheath.
Figure 9:
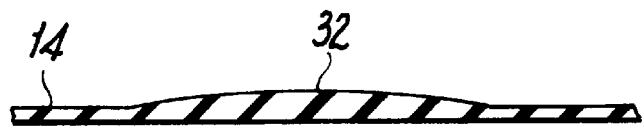
FIG. 9 is a cross-sectional view taken along section line 9—9 of FIG. 8.
Figure 10:
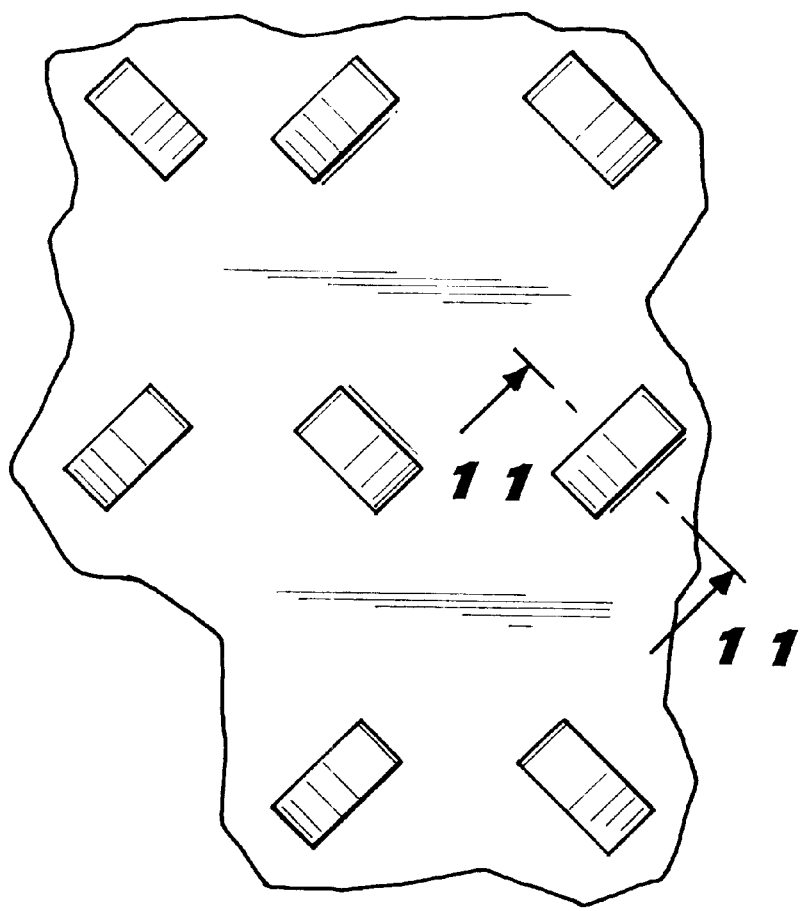
FIG. 10 is a top view of a portion of another alternative embodiment of the sheath.
Figure 11:
FIG. 11 is a cross-sectional view taken along section line 11—11 shown in FIG. 10.

Referring to FIGS. 6 and 7, sheath 14, when inflated, provides a seal along the entire length of the catheter between the outer surface thereof and the inner surface of the urethra. The sheath 14 may be further provided with at least one annular seal 30 which further seals the outer surface of sheath 14 against the inner wall of the urethra to prevent ascending infection. Preferably, multiple seals 30 are provided, with at least one being located adjacent the proximal end of sheath 14. Seal 30 may be formed by providing annular rings of reduced thickness in the sheath which are less capable of containing the pressure of inflation supplied through inlet tube 18. Thus, during inflation of sheath 14, the annular rings form a number of distended annular bulges which engage the urethra wall. Annular seals 30 may have varying configurations and/or dimensions so long as the required sealing is provided.

A multiplicity of bumps or projections 32 may also be formed on the external face of sheath 14 to aid in reducing slippage of sheath 14 against the urethra. As illustrated in FIGS. 8–11, projections 30 may have a variety of configurations, e.g., circular, rectangular, etc. Sheath 14 including bumps 32 may be formed by dipping a stainless steel mandrel having a multiplicity of depressions into rubber or latex and subsequently turning the sheath inside out so as to direct projections 32 radially outwardly.

Figure 2:
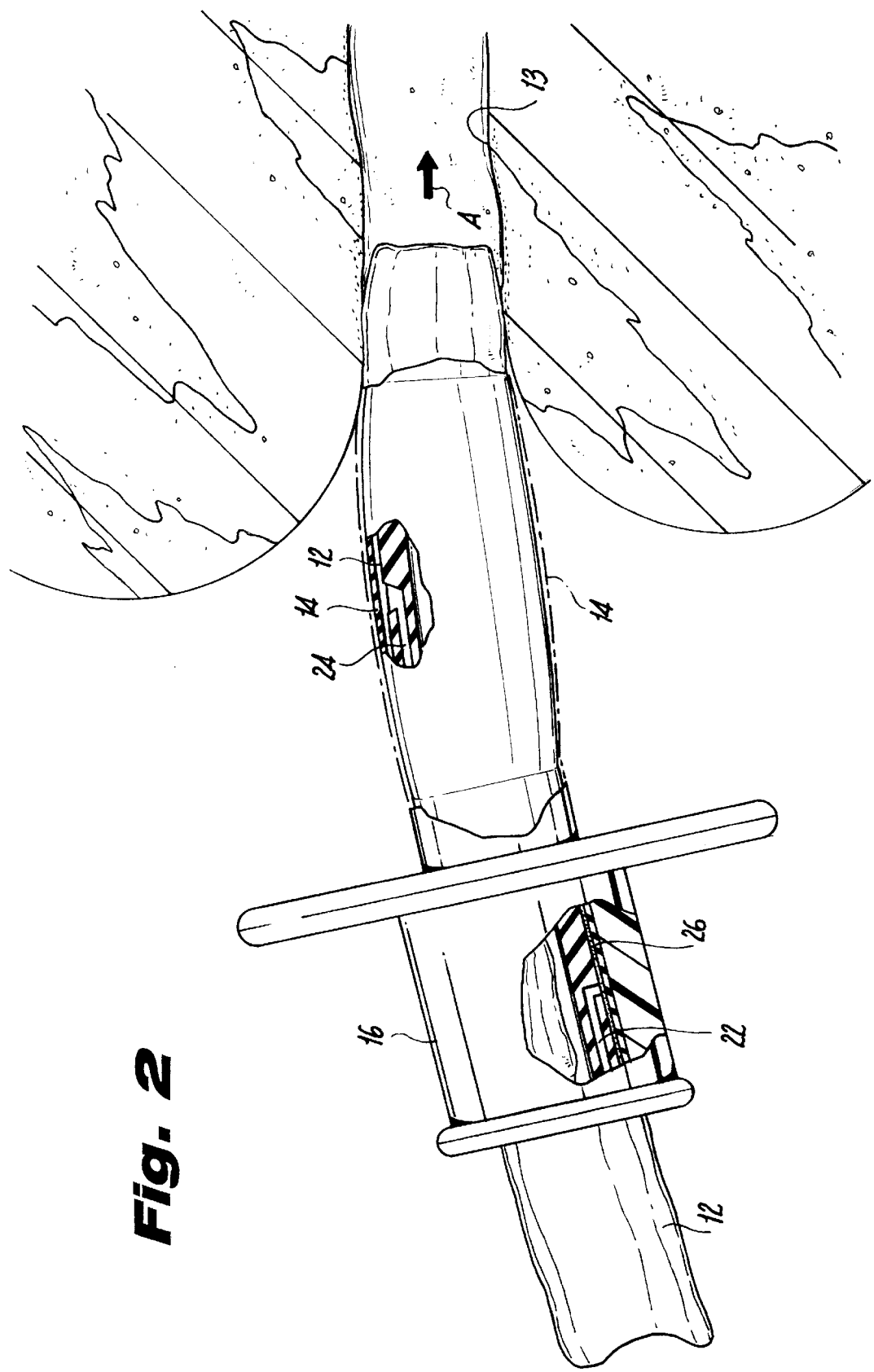
FIG. 2 is a side partial cross-sectional view of a distal portion of the drainage catheter system shown in FIG. 1, partially inserted into a patient's urethra.
Figure 3:
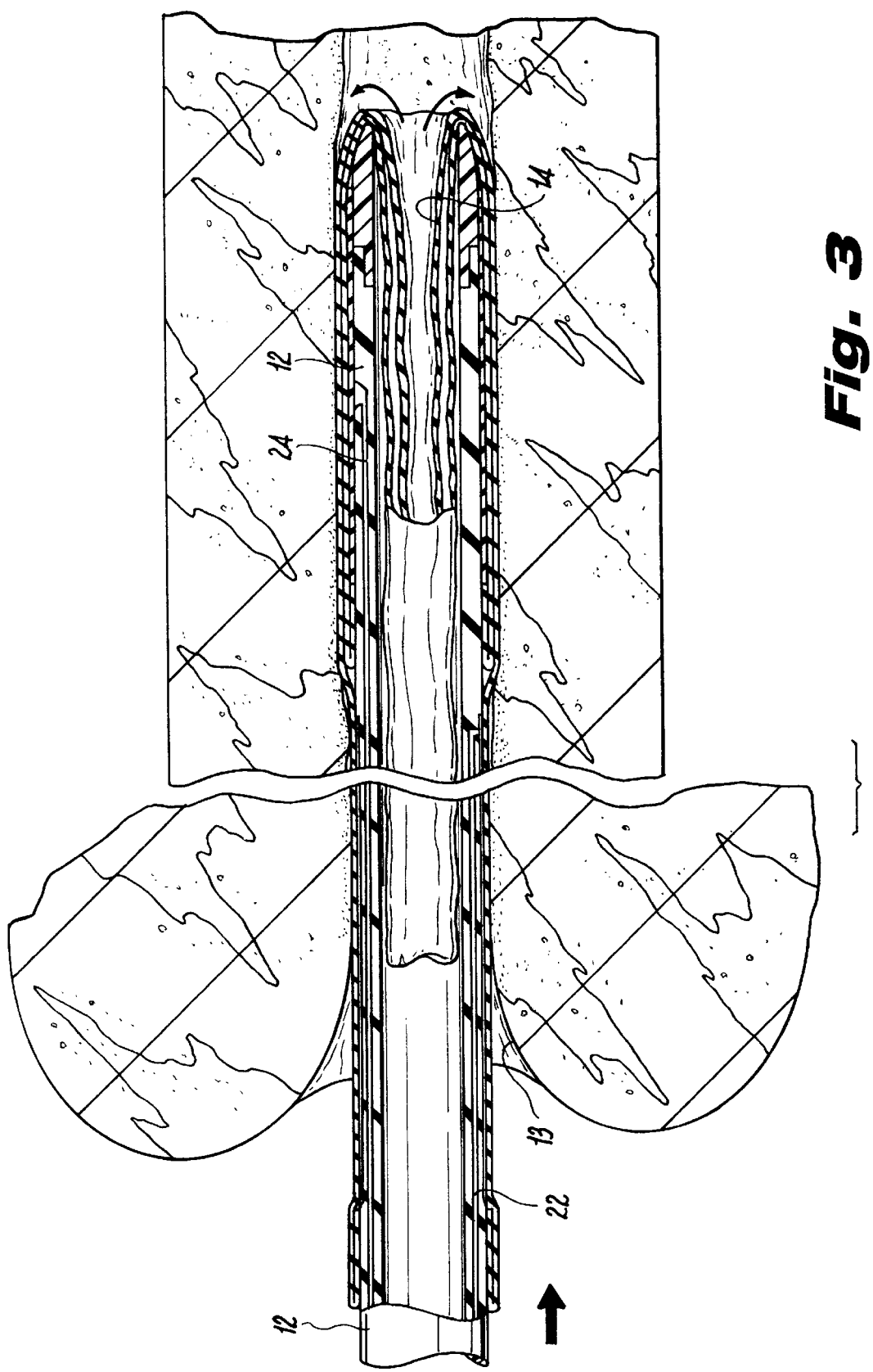
FIG. 3 is a side cross-sectional view of a distal end portion of the drainage catheter shown in FIG. 1, inserted in a patient's urethra.
Figure 4:
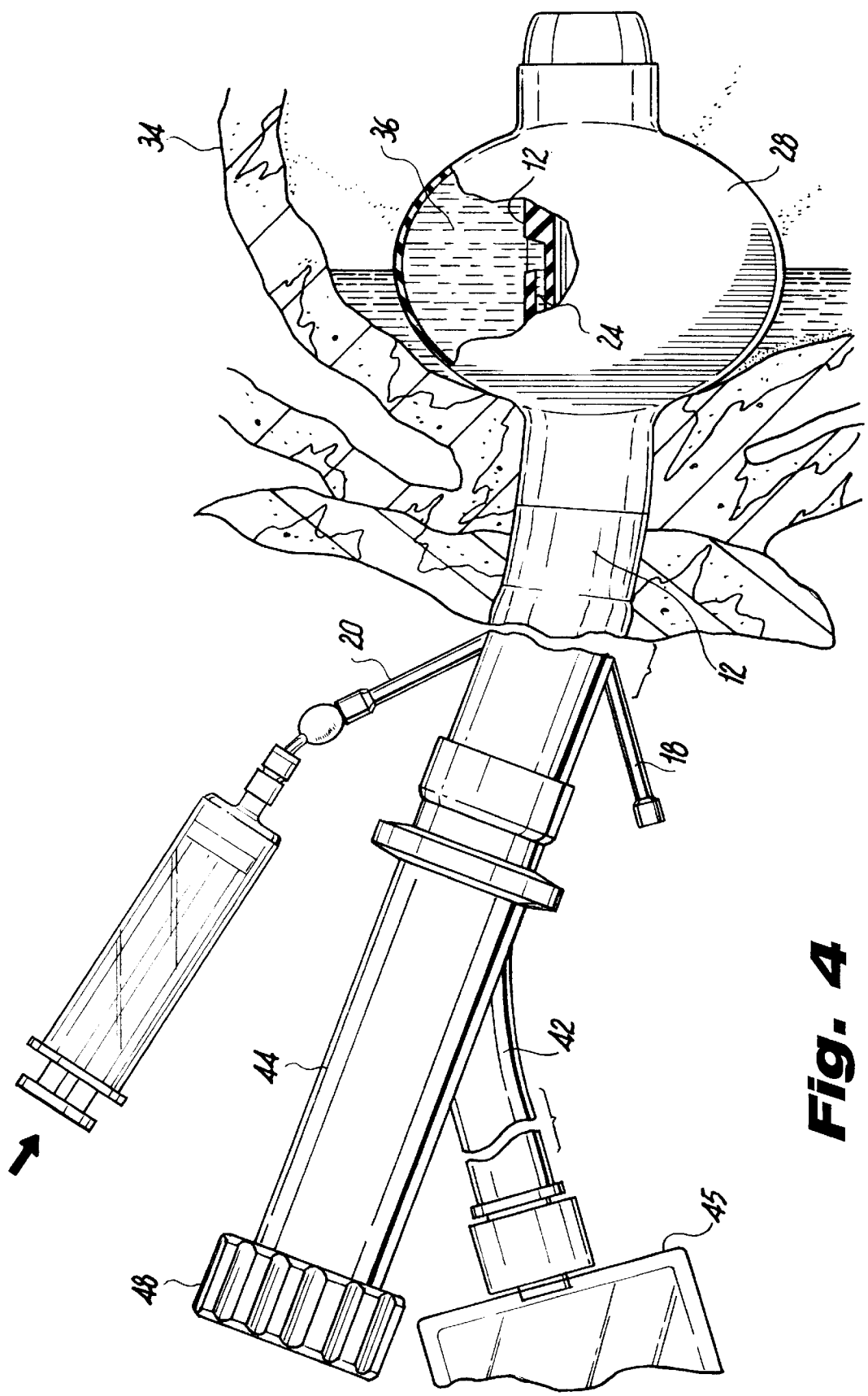
FIG. 4 is a side partial cross-sectional view of the drainage catheter system of FIG. 1, inserted in a patient's urethra with a retention balloon inflated.
Figure 5:
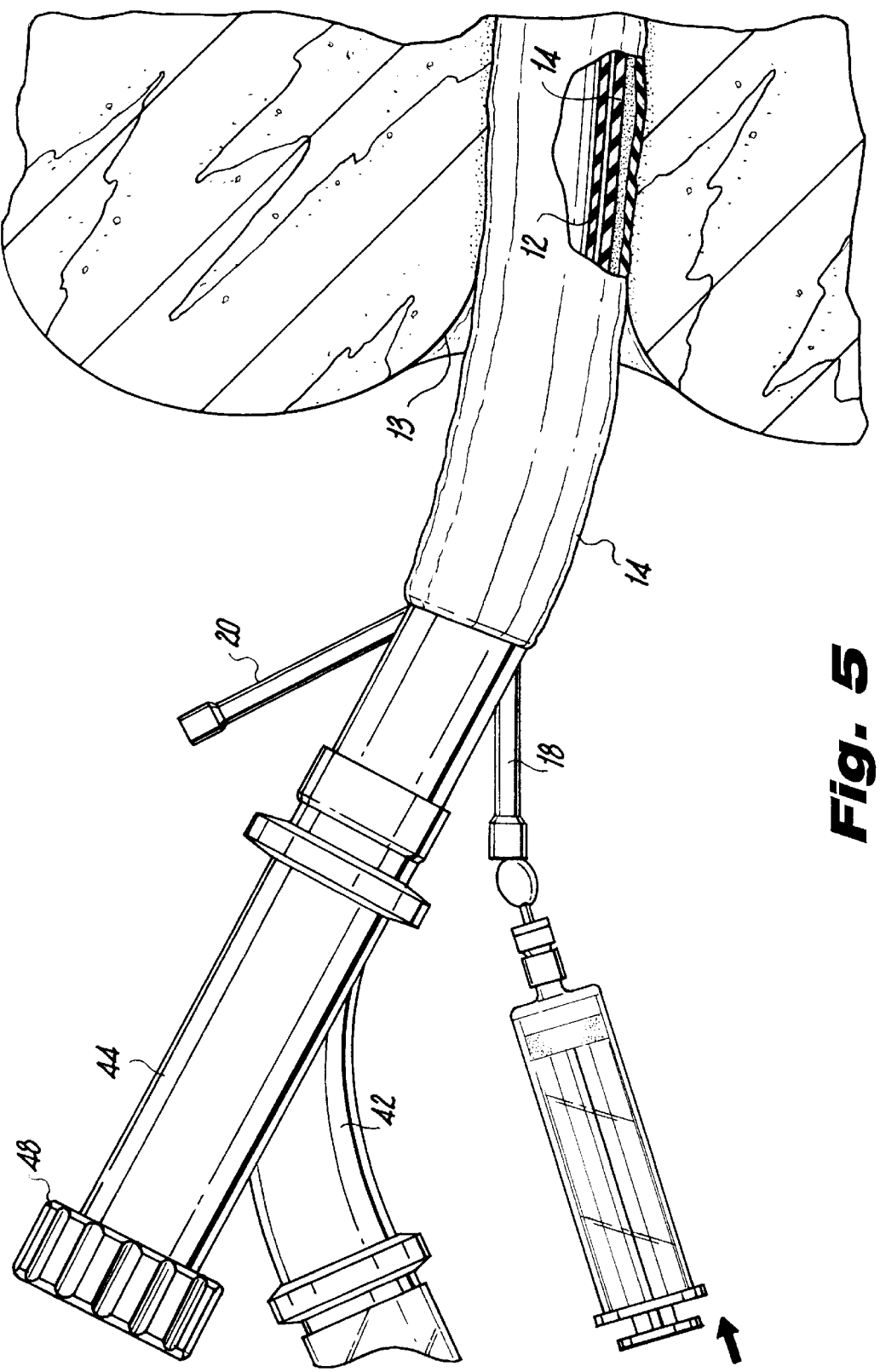
FIG. 5 is a side partial cross-sectional view of the proximal portion of the drainage catheter system shown in FIG. 1, with a fluid pressure source connected to an outlet tube.

Operation of drainage catheter system 10 will now be described with reference to FIGS. 2–5. Referring to FIG. 2, the distal end of drain tube 12 is inserted into the urethra 13, in the direction indicated by arrow "A", by grasping sheath grip 16, and pushing drain tube 12 therethrough. Referring to FIG. 3, as drain tube 12 is advanced through sheath grip 16, the distal end of tube 12 progressively deploys the sheath located within the drain tube 12 onto the inner wall of the urethra 13 to provide a path for itself as it is advanced towards the bladder 34 (FIG.4). Referring to FIG. 4, once the tip of drain tube 12 enters bladder 34, retention balloon 28 is inflated by supplying pressurized fluid 36 through second inlet tube 20 and second lumen 24, to secure drain tube 12 in place. Referring to FIG. 5, sheath 14 may also be inflated by supplying pressurized fluid 38 through first inlet tube 18 and first lumen 22, to provide the aforementioned air cushion between tube 12 and the inner wall of the urethra 13.

Referring now to FIGS. 12 and 13, drainage catheter system 10 further includes a connector member 40 secured to the proximal end of drain tube 12. Connector member 40 has a branch portion 42 adapted to be connected to a collection bag 45 (See FIG. 1) and an access portion 44 including an access port 46. A seal 48 is removably positioned within access port 46 and may be threadably fastened therein. A fluid diverter 50 is fastened to plug 48 such that when plug 48 is positioned within access port 46, diverter 50 is positioned to smoothly direct fluid into branch portion 42. Diverter 50 includes a key 52 which is configured to be received in a slot 54 formed in the access portion 44 to ensure proper alignment of diverter 50 in access portion 44.

Referring to FIGS. 14–16, drainage catheter system 10 further includes several accessory devices including an elongated bladder keeper, shown generally as 100 in FIG. 14. Elongated bladder keeper 100 includes an elongated body portion 102 dimensioned to extend through the length of drain tube 12, a cap retainer 104 having a seal 106, and a biasing member 108 positioned to bias a button 110 connected to the proximal end of body portion 102 to move body portion 102 proximally within tube 12. A diverter portion 103 of body portion 102 is positioned to direct fluid flow smoothly towards branch portion 42.

In use, elongated bladder keeper 100 is inserted through access port 46 in connector member 40 to a position adjacent the distal end of drain tube 12. Button 110 is pressed to advance elongated body portion 102 against the bias of member 108 to advance an engaging member 112 formed on the distal end of body portion 102 through the distal end of drain tube 12. Elongated bladder keeper 102 functions to prevent bladder 34 from sealing the open distal end of drain tube 12.

Another accessory device, a fluid introduction and clot auger, shown generally as 200, is illustrated in FIGS. 17–21. Fluid introduction and clot auger 200 includes an elongated body portion 202 insertable through access port 46 and drain tube 12. An auger blade 204 is formed on the outer surface of body portion 202. Body portion 202 is hollow and includes a milti-ported distal end 206. A proximal end of body portion 202 is adapted to receive a source of fluid 208. A cap retainer 210 is provided to rotatably secure fluid introduction and clot auger 200 to connector member 40. A knurled wheel 209 is secured to the proximal end of body portion 202 to facilitate rotation of auger blade 204. In use, a cleaning fluid, such as saline is supplied through body portion 202 and auger 204 is rotated within drain tube 12 to clean and remove clots and debris from drain tube 12.

Figure 22:
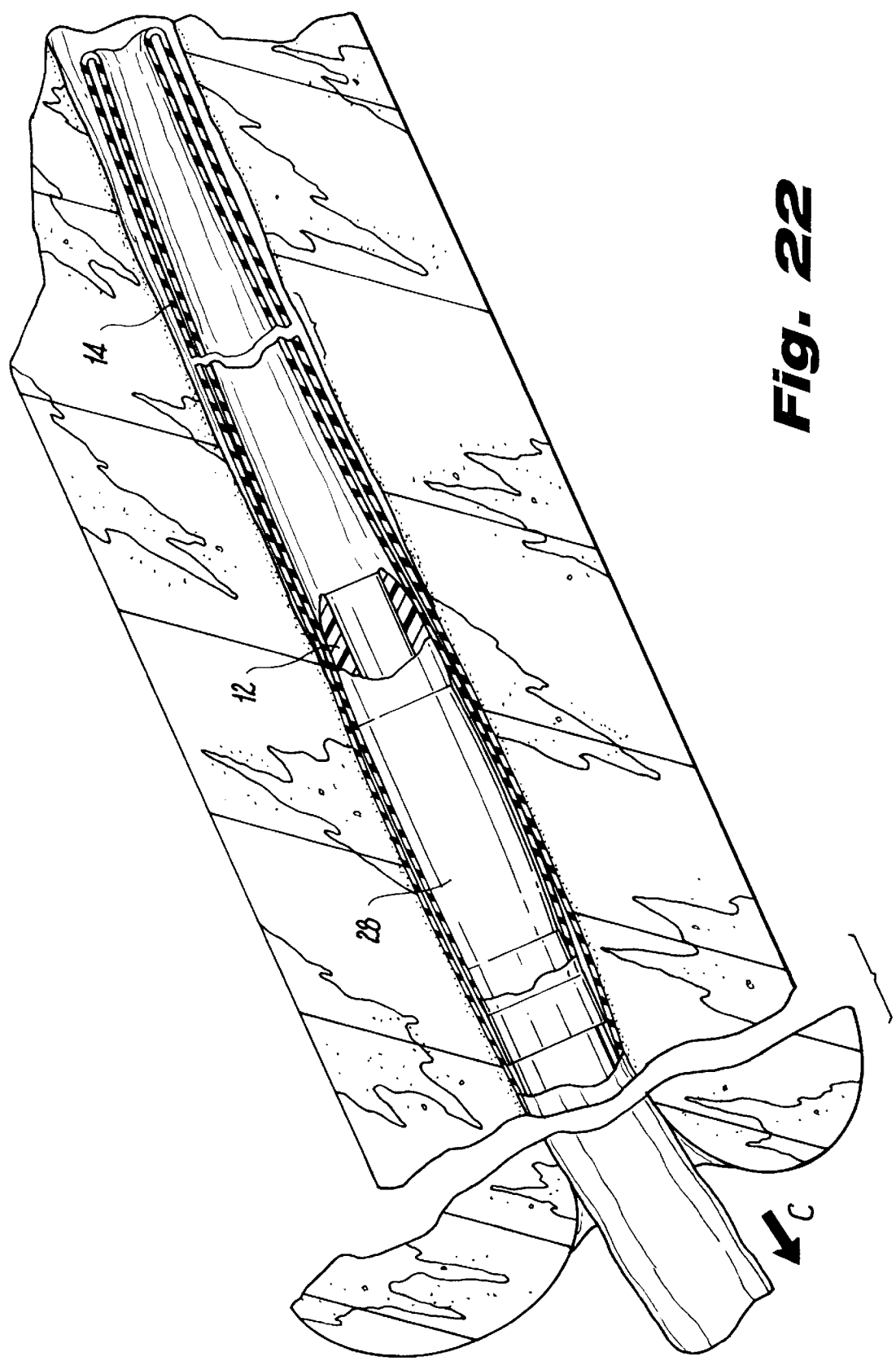
FIG. 22 is a side partial cross-sectional view of the distal end of the drainage catheter system shown in FIG. 1, as it is being removed from a patient's urethra.

Referring to FIG. 22, when the drainage catheter system 10 is no longer needed, the retention balloon 28 and the pressurized sheath 14 are deflated. As the drain tube 12 is pulled free, in the direction indicated by arrow "C", the flaccid sheath 14 peels away from the walls of the urethra and exits the patient following the drain tube 12.

Figure 23:
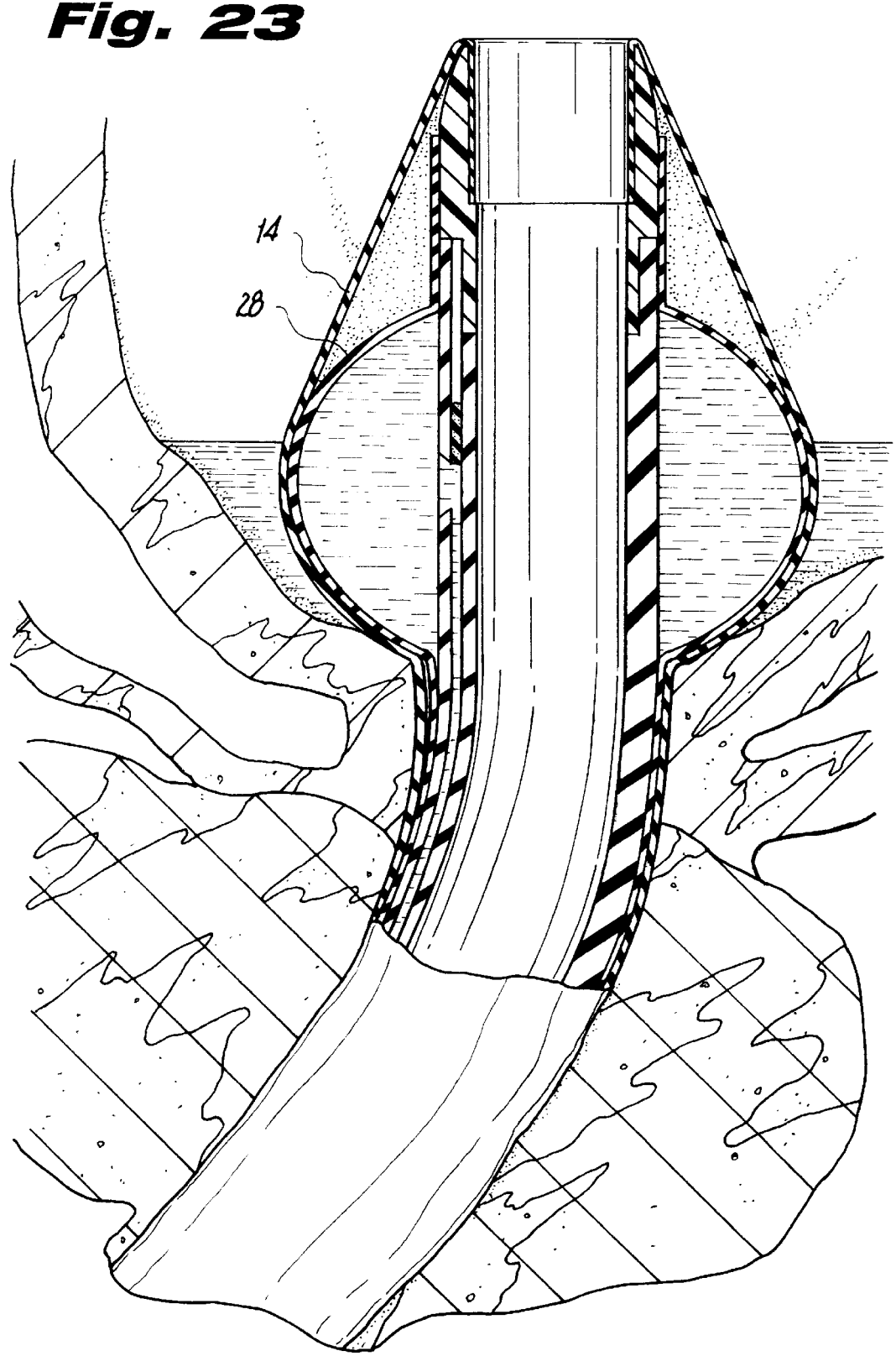
FIG. 23 is a partial cross-sectional view of a distal end of an alternate embodiment of a drainage catheter system.
Figure 24:
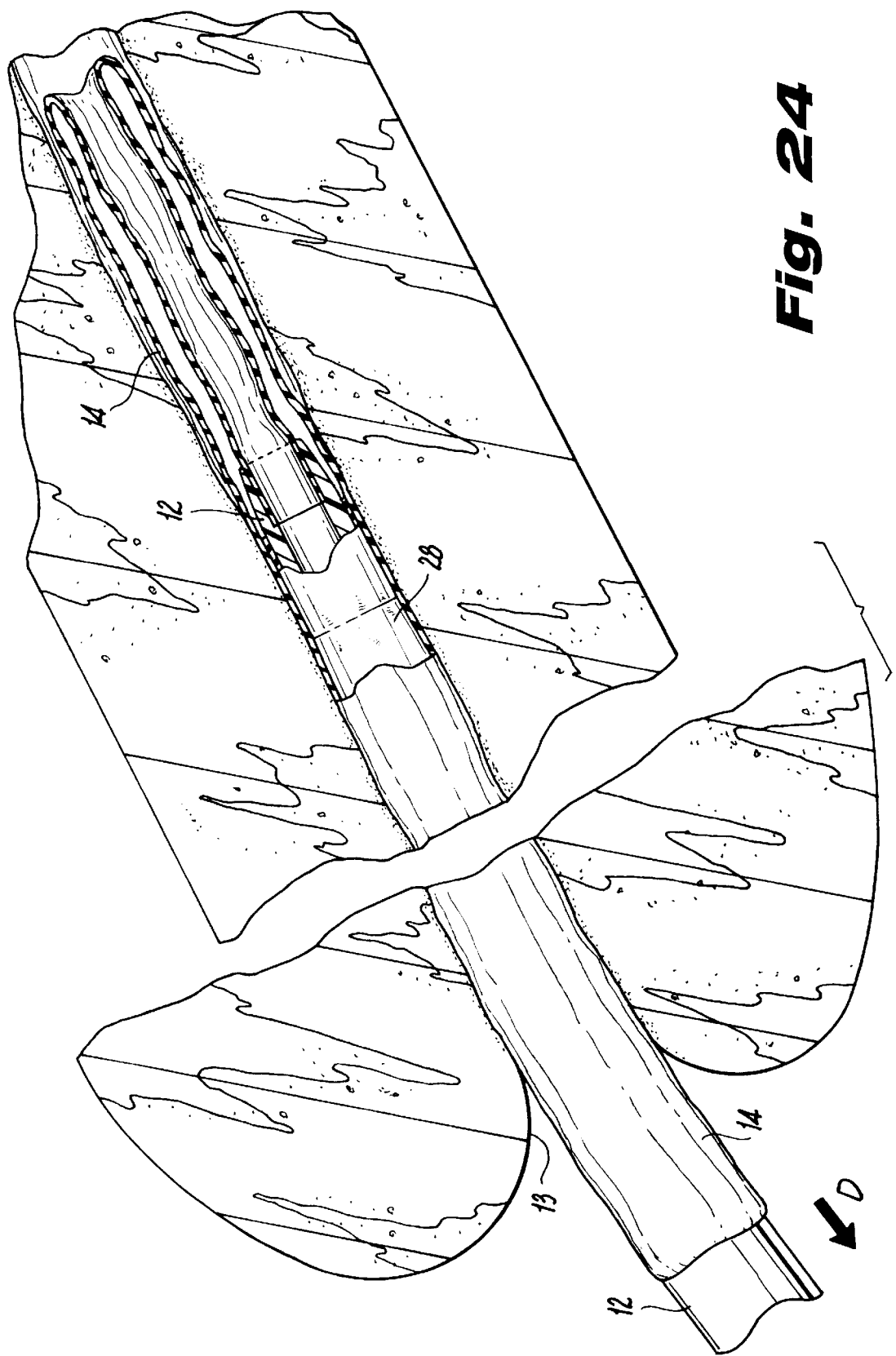
FIG. 24 is a partial cross-sectional view of the drainage catheter system shown in FIG. 23, being removed from a patient's urethra.

Referring now to FIGS. 23 and 24, in an alternate embodiment retention balloon 28 may be positioned between sheath 14 and drain tube 12. One end of sheath 14 is connected to the interior of the drain tube adjacent its distal end, while the opposite end of the sheath 14 is connected to the exterior of drain tube 12. Once again, as drain tube 12 is pulled from the urethra 13, in the direction indicated by arrow "D", the flaccid sheath peels away from the walls of the urethra and exits the patient following drain tube 12.

Figure 25:
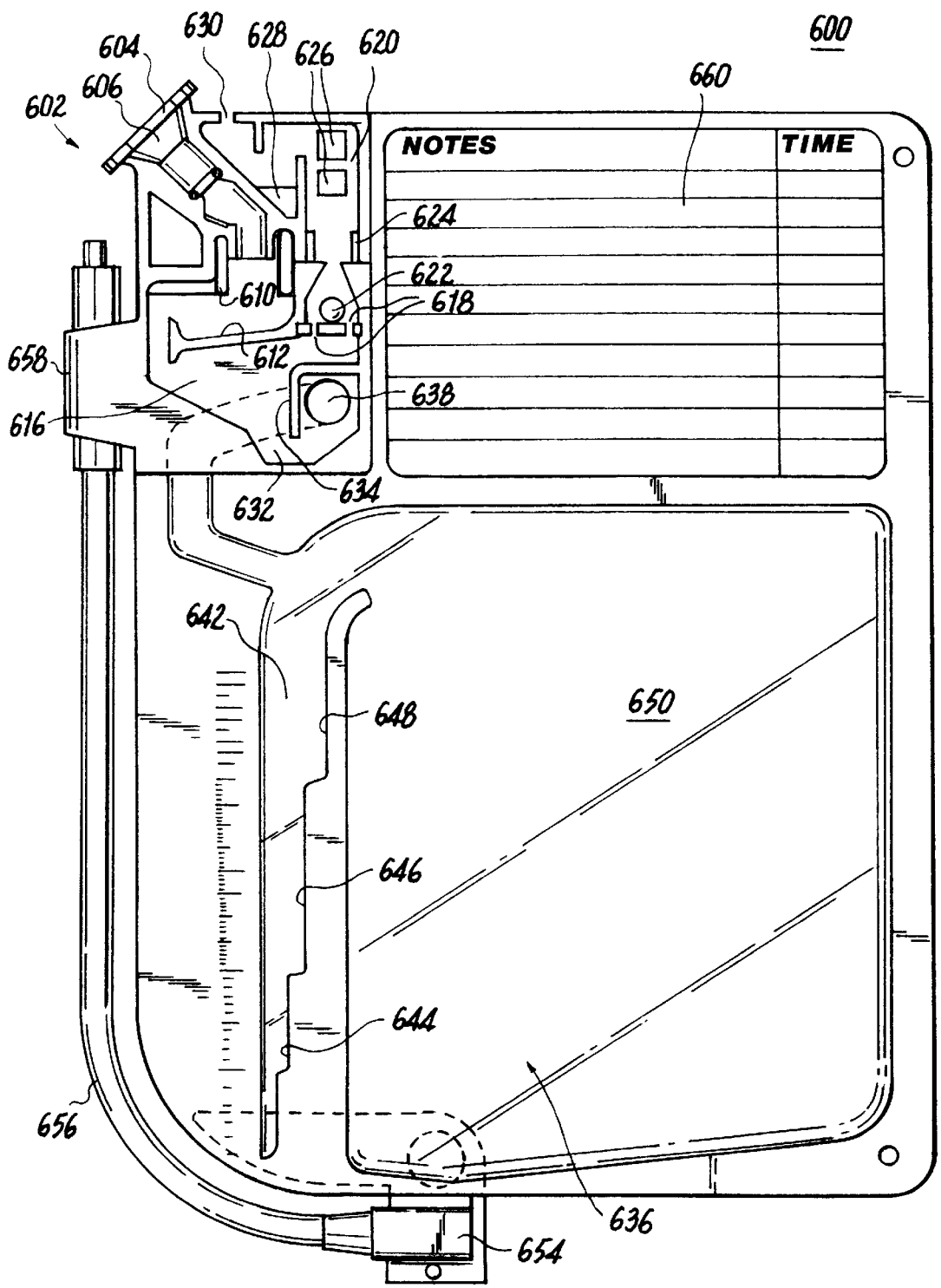
FIG. 25 is a side view of a collection bag constructed in accordance with a preferred embodiment of the invention.
Figure 26:
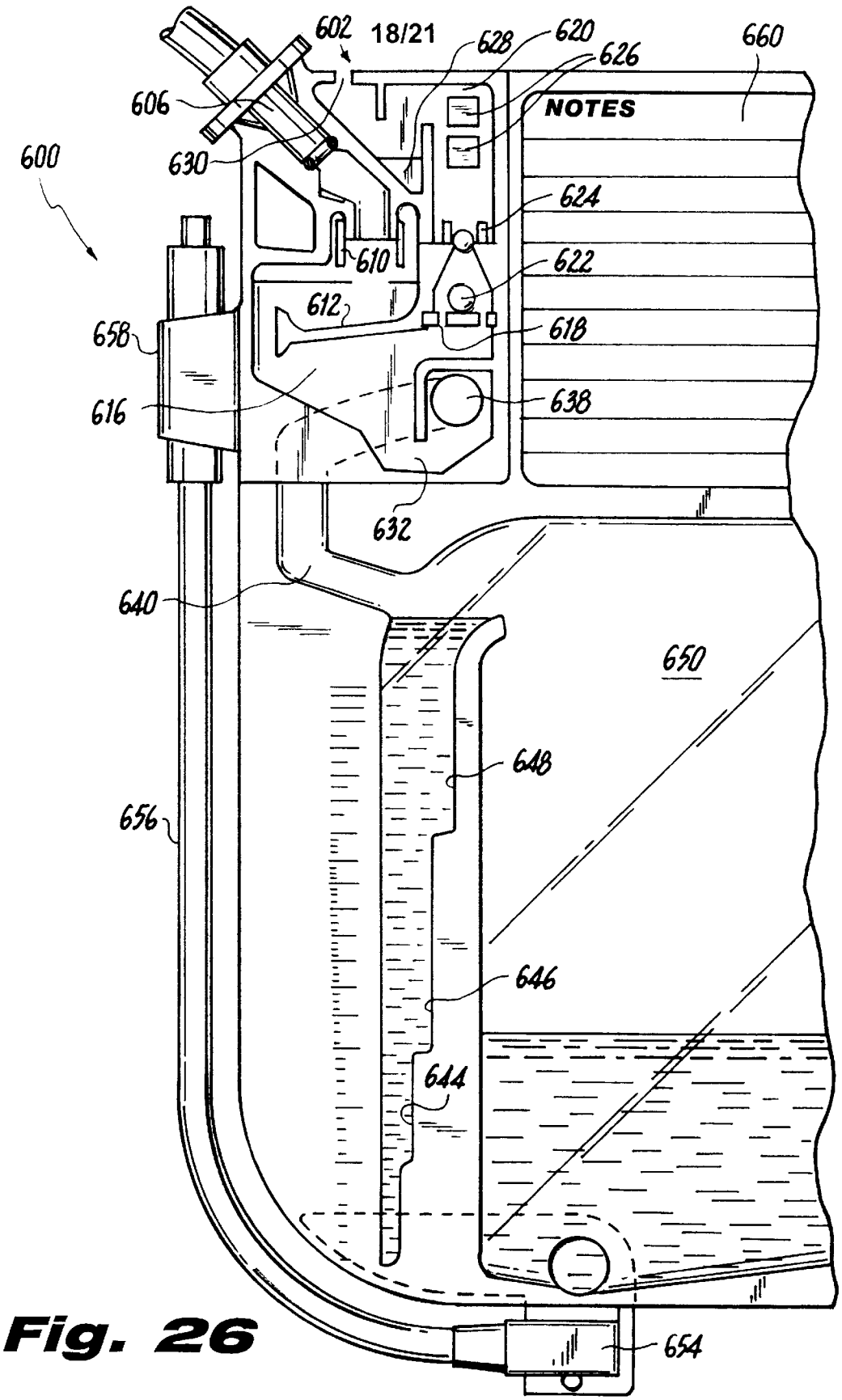
FIG. 26 is a side elevational view of a portion of the collection bag shown in FIG. 25.

Referring now to FIGS. 25 and 26, a novel collection bag 600 is illustrated for use with the catheter described above. It is also contemplated that this collection bag may be used with conventional drainage catheters already in use in the medical field. In addition, although shown as a urine collection bag, it is also envisioned that the novel features of this bag may be used to collect other fluids such as e.g. blood.

Collection bag 600 is preferably formed of a combination of light weight, inexpensive sheet plastics with injection molded components incorporated therein as discussed below. Other materials of construction may be substituted as needed depending upon application or design. The embodiments of collection bag 600 illustrated herein are adapted to be used in conjunction with a novel bag saddle described in detail hereinbelow. One skilled in the art will readily appreciate, however, that catheter bag 600 may be configured for use along with using conventional mounting structure such as, e.g. straps, surgical tape, etc.

Starting at the upper left hand side of collection bag 600, a fluid entry portion, shown generally at 602, is configured to be connected to a catheter drain. Preferably, fluid entry portion 602 is injection molded. Connector portion 604 is configured and dimensioned to receive a distal connector formed on the catheter drain. Preferably, this connector is a quick release connector designed for ease of operation by either hand. The neck 606 of connector portion 604 is flared to facilitate a secure press fit connection between the catheter connector and the fluid entry portion 602.

An acid pad 608 is disposed adjacent connector portion 604 such that urine entering the fluid entry portion 602 flows over pad 608. This feature serves to prevent crystallization of the urine which crystallization could inhibit the operation of subsequent valving structure described below. Preferably, the acid pad 608 is treated with ascorbic acid, however, one skilled in the art will appreciate that any urine soluble fluid which inhibits crystallization may be used.

After encountering acid pad 608, entering urine passes, by gravity, through one-way valve 610 and collects in observation pool 612. In this embodiment one-way valve 610 is configured as a flutter-type valve. However, any one-way valve which prevents accidental back flow of fluid may be substituted. Observation pool 612 is dimensioned to retain a small amount of "fresh" urine for direct visual observation and evaluation.

A drip ledge 614 allows excess urine to pass out of the observation pool 612 and drip into gas separation chamber 616. In this area, any gas carried with the liquid urine is permitted to vent from the system. Entrained gas moves upward through passages 618 into a gas test chamber 620. Interposed between pas separation chamber 616 and gas test chamber 620 are two valves. The first valve 622 is a floating ball valve designed to prevent accidental flow of liquid into the gas test chamber 620. The second valve 624, is a one way flutter valve for preventing back migration of gas from the gas test chamber 620 into the gas separation chamber 616. Second valve 624 also serves to prevent ambient air from entering and/or contaminating the closed system.

The gas test chamber 620 contains one or more indicator pads 626. These pads may contain indicators which signal the presence of, e.g. $CO_2$ or bacterial activity. After passing the gas test chamber 620, the gas is exposed to a deodorant 628 before venting through exit port 630 into the atmosphere.

Liquid, flowing over drip ledge 614, forms into droplets which may provide the attending physician with a urine drop count and estimation of urine flow in real time. As the liquid flows out of the observation pool 612 and into the gas separation chamber 620, it collects in a liquid collection chamber 632. An invert 634 extends downward into liquid collection chamber 632. This invert 634 forces gas venting from the liquid urine to remain in the gas separation chamber 620 and also provides a pathway through the liquid urine for gas generated in the main collection reservoir 636 described below. This provides the physician with a means for determining the situs of a bacteriological infection. For example, if the $CO_2$ gas is generated in the patient, the bubbles will be apparent on the left side of the invert 634. If, however, the bacterial contamination is in the collection bag itself, the $CO_2$ bubbles will appear on the right side of the invert 634.

Downstream of invert 634 is exit port 638 which directs the urine through passage 640 into the main collection reservoir 636. This reservoir 636 is provided with an initial graduated cavity 642 divided into predetermined volumetric levels 644–648. These volumetric levels preferably correspond to neonatal, infant, child, and adult levels, respectively. The initial graduated cavity 642 permits fine measurements of urine output. Preferably, initial graduated cavity 642 may be emptied into primary reservoir 650 by, for example, squeezing the cavity upward from the bottom. As shown in FIG. 26, once the graduated cavity 642 fills, the liquid urine passes into primary reservoir 650. An access port 652 is provided adjacent the bottom of primary reservoir 650 to allow for sampling and/or testing of the collected urine.

Drainage of the primary reservoir 650 is accomplished through drain 654 which is in fluid communication with the reservoir 650. An emptying hose 656 is attached to the drain 654 and serves as a conduit for the drained liquid. When not in use, hose 656 is snap fit into holder 658 on the side of the catheter bag.

Thus, combined with seals located adjacent the proximal end of the catheter, catheter bag 600 provides a closed system for draining fluid from a patient. This closed system effectively reduces or prevents contamination of specimens and/or patients from ambient conditions.

Catheter bag 600 may also be provided with a marking surface 660 for recording, e.g. patient data, flow readings, volume readings, etc.

Figure 27:
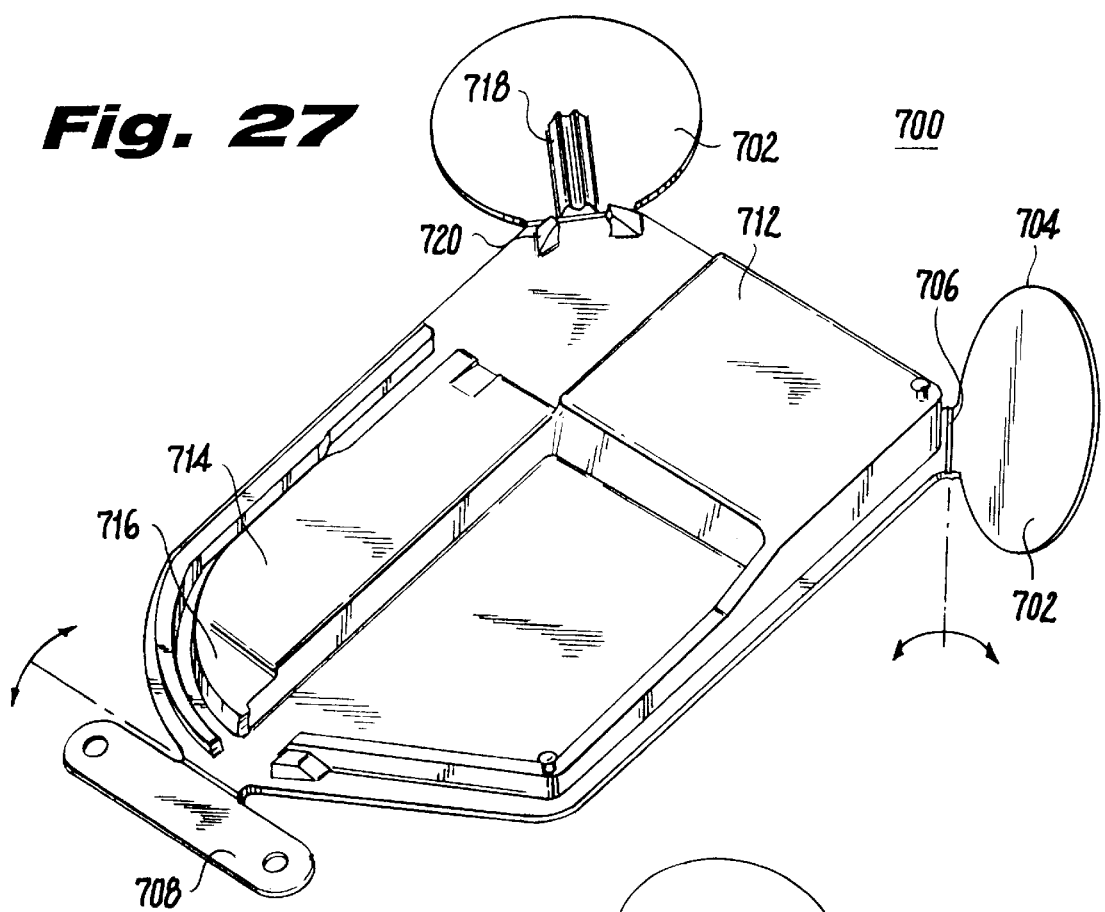
FIG. 27 is a top perspective view of a collection bag saddle constructed in accordance with the invention.
Figure 28:
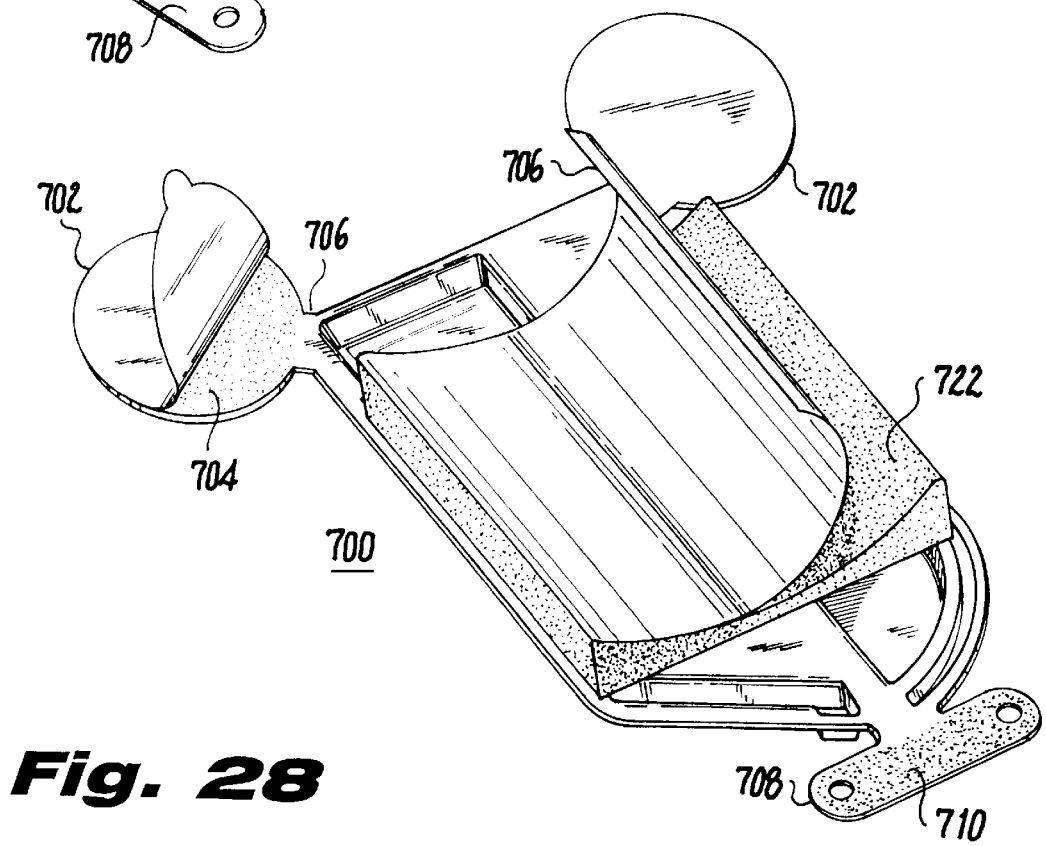
FIG. 28 is a bottom perspective view of the collection bag saddle shown in FIG. 27.

Referring now to FIGS. 27 and 28, a novel collection bag saddle is illustrated generally at 700. Although saddle 700 is specifically dimensioned to be used with collection bag 600 discussed above, novel features of saddle 700 may also be configured for use with conventional collection bags.

FIG. 27 illustrates a top perspective view of collection bag saddle 700. A pair of pads 702 are positioned adjacent opposite corners at the top portion of the saddle 700. These pads 702 are preferably provided with a biocompatible adhesive backing 704 (FIG. 28) which adheres to the patient's skin. Pads 702 are pivotably connected to the main body of saddle 700 in order to better facilitate positioning. This pivotable connection is shown as a living hinge 706 but may also be formed by other known pivoting structure. A channel 718 is formed in one pad and is configured to orient and hold the catheter in proper orientation. Another channel 720 is provided adjacent this pad to orient the fluid entry portion 602 of catheter bag 600.

Another pad 708 is pivotably mounted below the main body of the saddle 700. As with pads 702, it is preferred that a biocompatible adhesive 710 be applied on a back surface of the pad 708 to facilitate adhesion to the patient's skin.

Pads 702 and 708 serve to stabilize and mount the saddle 700 without the need for over application of adhesive tape. This mounting structure further minimizes the area of the skin which is in contact with the adhesive. Since saddle 700 can remain on the patient for extended periods, the discomfort associated with frequent removal of adhesive tape over large areas of skin when bags are removed is effectively eliminated.

The upper surface of the saddle 700 has a raised area 712 which provides a hard, flat surface below the collection bag 600 (See, FIG. 27) to permit written data entry thereon, e.g. in the marking surface 660 or other similar area provided on conventional collection bags (not shown). Another raised area 714 is provided adjacent the left side of the saddle 700 corresponding to the graduated cavity 642 of catheter bag 600. This raised area 714 provides a backing for recording liquid levels. In addition, when the physician elects to monitor very fine flow levels using catheter bag 600, after the graduated cavity has been filled, it may be emptied simply by placing pressure over choke point 716 and then compressing the cavity upward to evacuate the liquid. The graduated cavity is now configured to accurately measure liquid flow rates.

Referring to FIG. 28, the rear surface of the saddle 700 is faced with a biocompatible open cell foam 722 which allows air to circulate directly over the skin of the patient. This provides a more comfortable fit during periods of long term use.

Figure 29:
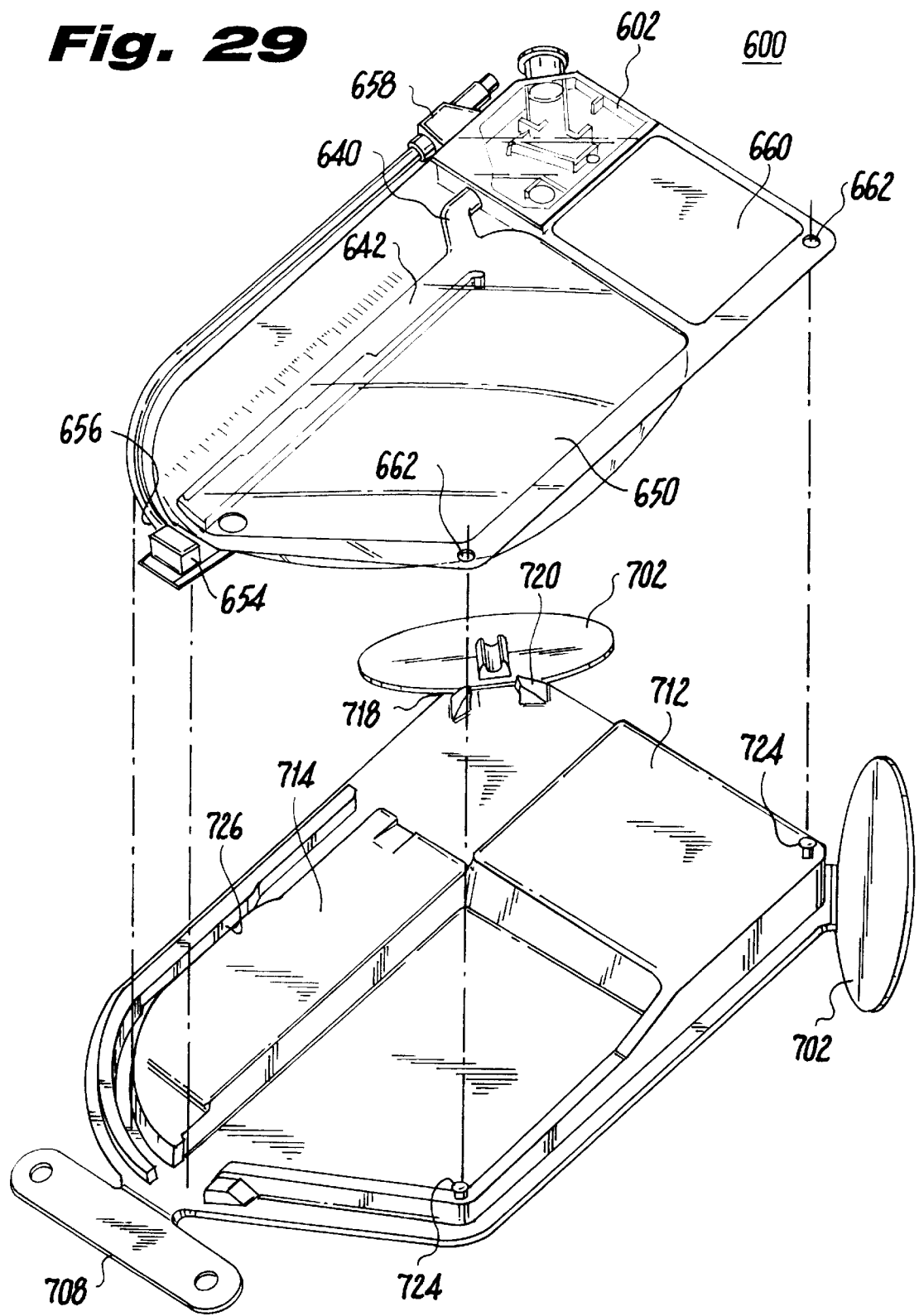
FIG. 29 is a top perspective view of the collection bag shown in FIG. 25 and the collection bag saddle shown in FIG. 27, in spaced apart alignment.

As illustrated in FIG. 29, the collection bag 600 has two main points of connection to saddle 700. One connection is adjacent the fluid entry portion 602 and the other is adjacent the drain 654. Both of these areas are preferably injection molded and have constricted areas which press fit into the saddle with minimal pressure. In addition, a pair of protrusions 724 are formed in saddle 700 and are configured to be received in mounting holes 662 of the catheter bag 600.

The bottom of the hose 656 is retained and controlled at the base of the bag 600 by its attachment to the injection molded at the drain 654. The top of the drain hose is secured by holder 658 formed into the catheter bag 600 while the mid-portion of the hose 656 is positioned in hose channel 726 formed in the saddle 700.

Figure 30:
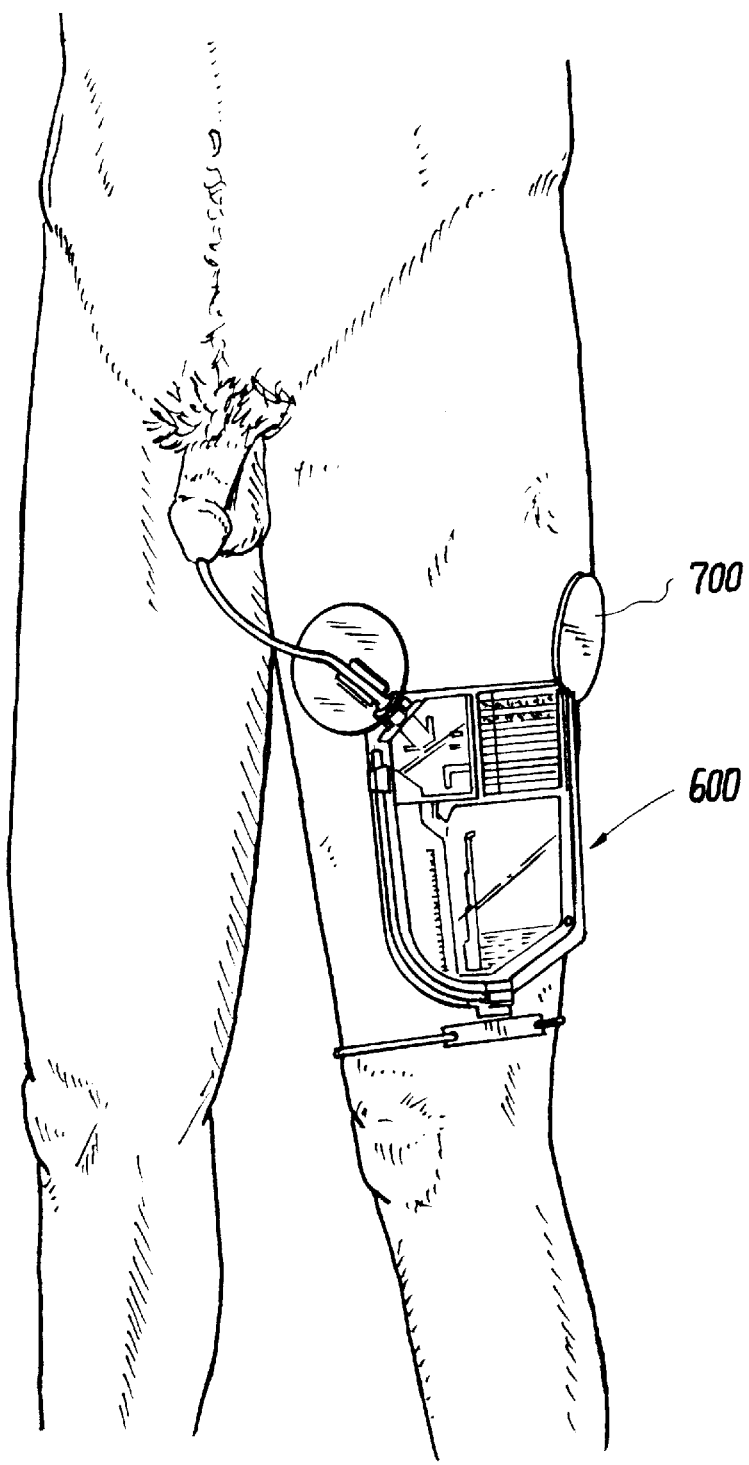
FIG. 30 is a side perspective view of the collection bag of FIG. 25 and collection bag saddle of FIG. 27, secured to a patient.

FIG. 30 illustrates a catheter bag 600/saddle 700 combination in position on a patient. The saddle 700 is secured to the patient's thigh and the bag 600 is easily removable therefrom to facilitate change without the need to re-position the bag.

These and other features of the subject invention will be readily apparent to one having ordinary skill in the art from the drawings and photographs which accompany this disclosure. The above description should not be construed as limiting, but merely as exemplifications of preferred embodiments. Moreover, various modifications may be made to the embodiments disclosed herein. For example, the acid pad, which prevents crystallization which may inhibit operation of subsequent valving structure, may be positioned at any location suitable to perform this function, such as, downstream of the observation pool. Those skilled in the art will envision other modifications within the scope and spirit of the claims appended hereto.

What is claimed is:

1. A drainage catheter system comprising:

a) a urethral catheter including an elongate catheter body having an interior lumen extending therethrough defined by an interior surface and having an exterior surface, an elongate tubular sheath operatively associated with said catheter body and having opposed first and second ends, the first and second ends of said sheath supported adjacent the exterior surface of said catheter body, and a layer of lubricant sealingly disposed between said sheath and said catheter body along the interior and exterior surfaces thereof to reduce frictional resistance between said sheath and said catheter body;

b) a closed system collection bag communicating with said urethral catheter including a fluid entry portion defining a fluid conduit, the conduit having a one-way fluid valve in line to prevent back flow of fluid and a gas separation chamber for venting gas to the atmosphere, said fluid entry portion further including at least one one-way gas valve for preventing entry of ambient air into the collection bag, a main liquid reservoir in fluid communication with the fluid entry portion for receiving and storing liquid therein, and a sealed drainage member in fluid communication with the main liquid reservoir for permitting drainage of the main liquid reservoir; and c) a collection bag saddle for securing said collection bag to a patient, said collection bag saddle including a main body portion, a plurality of mounting pads attached to the main body portion, the mounting pads having adhesive backing thereon for adherence to a patient's skin, and collection bag mounting structure formed in the main body portion for releasably mounting the collection bag thereon.

2. A drainage catheter system which comprises:
a) an elongate catheter body dimensioned for insertion into a patient's urethra, said elongate catheter body having an interior lumen extending therethrough defined by an interior surface and having an exterior surface;
b) an elongate tubular sheath operatively associated with said catheter body and having opposed first and second ends, the first and second ends of said sheath being positioned adjacent the exterior surface of said catheter body and said sheath being supported by said catheter body to facilitate progressive deployment of the elongate tubular sheath from within the interior lumen of the catheter body during insertion of the catheter body into a patient's urethra; and
c) a layer of lubricant sealingly disposed between said sheath and said catheter body along the interior and exterior surfaces thereof to reduce frictional resistance between said sheath and said catheter body.

3. A drainage catheter system as recited in claim 2, wherein said tubular sheath includes at least one annular seal located on said tubular sheath.

4. A drainage catheter system as recited in claim 3, wherein said at least one annular seal includes a plurality of annular seals.

5. A drainage catheter system as recited in claim 2, further including an access port in communication with the interior lumen and having a removable seal.

6. A drainage catheter system as recited in claim 2, further including an elongated bladder keeper having an elongated body extending through said catheter body, said elongated body having an engaging member positioned adjacent a distal end of said catheter body.

7. A drainage catheter system as recited in claim 6, wherein said elongated body is reciprocable within said catheter body from a first position in which said engaging member is located substantially within said catheter body to a second position in which said engaging member is located substantially outside of said catheter body.

8. A drainage catheter system as recited in claim 2, further including a fluid introduction and clot auger including an elongated body portion rotatably supported within said catheter body, said body portion being hollow and being adapted to receive a fluid flow, said body portion further including an auger blade positioned along the exterior of said body portion.

9. A drainage catheter system as recited in claim 8, wherein said body portion includes at least one distal opening to facilitate fluid flow therethrough.

10. A drainage catheter system which comprises:
a) an elongate catheter body having an interior lumen extending therethrough defined by an interior surface and having an exterior surface;
b) an elongate tubular sheath operatively associated with said catheter body and having opposed first and second ends, the first and second ends of said sheath supported adjacent the exterior surface of said catheter body;
c) a layer of lubricant sealingly disposed between said sheath and said catheter body along the interior and exterior surfaces thereof to reduce frictional resistance between said sheath and said catheter body; and
further including a grip member positioned adjacent said exterior surface of said catheter body, said grip member being movable relative to said catheter body.

11. A drainage catheter system as recited in claim 10, wherein said second end of said tubular sheath is supported by said grip member adjacent said exterior surface of said catheter body.

12. A drainage catheter system which comprises:
a) an elongate catheter body having an interior lumen extending therethrough defined by an interior surface and having an exterior surface;
b) an elongate tubular sheath operatively associated with said catheter body and having opposed first and second ends, the first and second ends of said sheath supported adjacent the exterior surface of said catheter body; and
c) a layer of lubricant sealingly disposed between said sheath and said catheter body along the interior and exterior surfaces thereof to reduce frictional resistance between said sheath and said catheter body,
wherein said tubular sheath includes a multiplicity of bumps to reduce slippage between said tubular sheath and a patient's urethra.

13. A drainage catheter system which comprises:
a) an elongate catheter body having an interior lumen extending therethrough defined by an interior surface and having an exterior surface;
b) an elongate tubular sheath operatively associated with said catheter body and having opposed first and second ends, the first and second ends of said sheath supported adjacent the exterior surface of said catheter body;
c) a layer of lubricant sealingly disposed between said sheath and said catheter body along the interior and exterior surfaces thereof to reduce frictional resistance between said sheath and said catheter body; and
further including means for inflating said tubular sheath.

14. A drainage catheter system as recited in claim 13, wherein said means for inflating includes a passage in the catheter body having a first end adapted to communicate with a pressure source and a second end communicating with a space between said catheter body and said tubular sheath.

15. A drainage catheter system which comprises:
a) an elongate catheter body having an interior lumen extending therethrough defined by an interior surface and having an exterior surface; and
b) an elongate lubricated tubular sheath operatively associated with said catheter body and having opposed first and second ends, the first and second ends of said lubricated sheath supported adjacent the exterior surface of said catheter body, a substantial portion of said lubricated sheath disposed within the interior lumen of said catheter body prior to insertion of the catheter assembly into the urethra, whereby the lubricated sheath is progressively deployed from the interior lumen of the catheter body as the catheter assembly is inserted into the urethra, to continuously enclose the exterior surface of the catheter body, and upon becoming fully deployed, the lubricated sheath permitting movement of the catheter body relative to the urethra without causing trauma thereto.

16. A drainage catheter system as recited in claim 15, further including a grip member positioned adjacent said exterior surface of said catheter body, said grip member being movable relative to said catheter body.

17. A drainage catheter system as recited in claim 16, wherein said second end of said tubular sheath is supported by said grip member adjacent said exterior surface of said catheter body.

18. A drainage catheter system as recited in claim 15, wherein said tubular sheath includes at least one annular seal located on said tubular sheath.

19. A drainage catheter system as recited in claim 18, wherein said at least one annular seal includes a plurality of annular seals.

20. A drainage catheter system as recited in claim 15, wherein said tubular sheath includes a multiplicity of bumps to reduce slippage between said tubular sheath and a patient's urethra.

21. A drainage catheter system as recited in claim 15, further including an access port in communication with the interior lumen and having a removable seal.

22. A drainage catheter system as recited in claim 15, further including an elongated bladder keeper having an elongated body extending through said catheter body, said elongated body having an engaging member positioned adjacent a distal end of said catheter body.

23. A drainage catheter system as recited in claim 22, wherein said elongated body is reciprocable within said catheter body from a first position in which said engaging member is located substantially within said catheter body to a second position in which said engaging member is located substantially outside of said catheter body.

24. A drainage catheter system as recited in claim 15, further including a fluid introduction and clot auger including an elongated body portion rotatably supported within said catheter body, said body portion being hollow and being adapted to receive a fluid flow, said body portion further including an auger blade positioned along the exterior of said body portion.

25. A drainage catheter system as recited in claim 24, wherein said body portion includes at least one distal opening to facilitate fluid flow therethrough.

26. A drainage catheter system as recited in claim 15, further including means for inflating said tubular sheath.

27. A drainage catheter system as recited in claim 26, wherein said means for inflating includes a passage in the catheter body having a first end adapted to communicate with a pressure source and a second end communicating with a space between said catheter body and said tubular sheath.

28. A closed system collection bag comprising:
a fluid entry portion defining a fluid conduit, the conduit having a one-way fluid valve in line to prevent back flow of fluid and a gas separation chamber for venting gas to the atmosphere, said fluid entry portion further including at least one one-way gas valve for preventing entry of ambient air into the collection bag;
a main liquid reservoir in fluid communication with the fluid entry portion for receiving and storing liquid therein; and
a sealed drainage member in fluid communication with the main liquid reservoir for permitting drainage of the main liquid reservoir.

29. A collection bag saddle comprising:
a main body portion;
a plurality of mounting pads attached to the main body portion, the mounting pads having adhesive backing thereon for adherence to a patient's skin; and
collection bag mounting structure supported by the main body portion, the collection bag mounting structure being configured to releasably mount a collection bag thereon.

* * * * *